US007723293B2

(12) United States Patent
Hempstead et al.

(10) Patent No.: US 7,723,293 B2
(45) Date of Patent: May 25, 2010

(54) METHODS FOR INCREASING CAPILLARY DENSITY AND MAINTAINING VIABILITY OF MICROVASCULAR CARDIAC ENDOTHELIAL CELLS USING TRK RECEPTOR LIGANDS

(75) Inventors: Barbara L. Hempstead, New York, NY (US); Rosemary Kraemer, Brooklyn, NY (US); Shahin Rafii, Great Neck, NY (US); Phi Wiegn, New York, NY (US); Michael L. Donovan, Brookline, MA (US)

(73) Assignees: Cornell Research Foundation, Inc., Ithaca, NY (US); Children's Medical Center Corporation, Boston, MA (US)

(*) Notice: Subject to any disclaimer, the term of this patent is extended or adjusted under 35 U.S.C. 154(b) by 502 days.

(21) Appl. No.: 11/589,659

(22) Filed: Oct. 30, 2006

(65) Prior Publication Data

US 2007/0110735 A1 May 17, 2007

Related U.S. Application Data

(63) Continuation of application No. 09/830,520, filed as application No. PCT/US99/25365 on Oct. 28, 1999, now abandoned.

(60) Provisional application No. 60/119,994, filed on Feb. 12, 1999, provisional application No. 60/105,928, filed on Oct. 28, 1998.

(51) Int. Cl.
*A61K 38/18* (2006.01)
(52) U.S. Cl. ............................... 514/2; 514/12; 530/399
(58) Field of Classification Search ........................ None
See application file for complete search history.

(56) References Cited

U.S. PATENT DOCUMENTS

| | | | |
|---|---|---|---|
| 4,119,618 A | 10/1978 | Said | |
| 5,180,820 A | 1/1993 | Barde et al. | |
| 5,229,500 A | 7/1993 | Barde et al. | |
| 5,235,043 A | 8/1993 | Collins et al. | |
| 5,338,840 A | 8/1994 | Bayne et al. | |
| 5,401,832 A | 3/1995 | Linemeyer et al. | |
| 5,438,121 A | 8/1995 | Barde et al. | |
| 5,453,361 A | 9/1995 | Yancopoulos et al. | |
| 5,488,099 A | 1/1996 | Persson et al. | |
| 5,512,661 A | 4/1996 | Shooter et al. | |
| 5,534,615 A | 7/1996 | Baker et al. | |
| 5,654,427 A | 8/1997 | Dionne et al. | |
| 5,665,862 A | 9/1997 | Fischbach et al. | |
| 5,672,683 A | 9/1997 | Friden et al. | |
| 5,712,395 A | 1/1998 | App et al. | |
| 5,733,727 A | 3/1998 | Field | |
| 5,733,871 A | 3/1998 | Alps et al. | |
| 5,739,113 A | 4/1998 | Lee | |
| 5,747,655 A | 5/1998 | Johnson, Jr. et al. | |
| 5,750,373 A | 5/1998 | Garrard et al. | |
| 5,763,441 A | 6/1998 | App et al. | |
| 5,763,584 A | 6/1998 | Godowski | |
| 5,770,577 A | 6/1998 | Kinstler et al. | |
| 5,817,471 A | 10/1998 | Kaplan et al. | |

FOREIGN PATENT DOCUMENTS

| | | |
|---|---|---|
| WO | WO 95/21193 | 8/1995 |
| WO | WO 96/33731 | 10/1996 |
| WO | WO 97/21732 | 6/1997 |
| WO | WO 98/13071 | 4/1998 |
| WO | WO 98/32859 | 7/1998 |
| WO | WO 98/49300 | 11/1998 |
| WO | WO 99/06073 | 2/1999 |
| WO | WO 99/21590 | 5/1999 |
| WO | WO 99/26480 | 6/1999 |
| WO | WO 99/40945 | 8/1999 |
| WO | WO 99/50403 | 10/1999 |
| WO | WO 00/10552 | 3/2000 |

OTHER PUBLICATIONS

Oikawa et al., "Inhibition of Angiogenesis by Staurosporine, A Potent Protein Kinase Inhibitor," *The Journal of Antibiotics*, 45(7):1155-1160 (1992).
Hardie, eds. *The Protein Kinase Factsbook II: Protein-Tyrosine Kinases*, London:Academic Press, pp. 208-217 (1995).
Hempstead, "Strategies for Modulating Trk Receptor Activity," *Experimental Neurology*, 124:31-36 (1993).
Hempstead et al., "Brain Derived Neurotropic Factor Induces Angiogenesis: Role in Intramyocardial Vessel Development," *Blood*, 92(10) Suppl. 1 Part 1-2:175A, 40th Annual Meeting of Am. Soc. Hematol. (1998) (abstract only).
McGregor et al., "Roles of Trk Family Neurotrophin Receptors in Medullary Thyroid Carcinoma Development and Progression," *Proc. Natl. Acad. Sci. USA*, 96:4540-4545 (1999).
Donovan et al., "Neurotrophin and Neurotrophin Receptors in Vascular Smooth Muscle Cells," *American Journal of Pathology*, 147(2):309-324 (1995).

(Continued)

*Primary Examiner*—Christine J Saoud
(74) *Attorney, Agent, or Firm*—Nixon Peabody LLP

(57) ABSTRACT

The present invention relates to methods of inducing or inhibiting the angiogenic process and promoting vessel growth or stabilization in an organ by modulating the trk receptor pathway. The present invention also relates to a method for treating a pathological disorder in a patient which includes administering a trk receptor ligand or an inhibitor or expression or activity of a trk receptor ligand. The present invention also relates to a method of screening for a modulator of angiogenesis, vessel growth, or vessel stabilization. Another aspect of the present invention is a method of diagnosing or monitoring a pathological disorder in a patient which includes determining the presence or amount of a trk receptor ligand or activation of a trk receptor ligand in a biological sample.

11 Claims, 10 Drawing Sheets

OTHER PUBLICATIONS

Witzke et al., "Myocardial Ultrastructural Changes Induced by Administration of Nerve Growth Factor," in Gardner, ed., *Surgical Forum*, vol. XXVII, Chicago, Illinois:American College of Surgeons, pp. 295-297 (1976).

Kaye et al., "Nerve Growth Factor-Enhanced Reinnervation of Surgically Denervated Canine Heart," *Am. J. Physiol.*, 236(4):H624-H628 (1979).

Long et al., "Trophic Factors for Cardiac Myocytes," *Journal of Hypertension*, 8 (suppl 7):S219-S224 (1990).

Santos et al., "Nerve Growth Factor: Increased Angiogenesis Without Improved Nerve Regeneration," *Otolaryngol. Head Neck Surg.*, 105:12-25 (1991).

Scarisbrick et al., "Coexpression of mRNAs for NGF, BDNF, and NT-3 in the Cardiovascular System of the Pre- and Postnatal Rat," *J. Neurosci.*, 13(3):875-893 (1993).

Tsukahara et al., "The Role of Brain-Derived Neurotrophic Factor in Transient Forebrain Ischemia in the Rat Brain," *Neurosurgery*, 34:323-331 (1994).

Hassankhani et al., "Overexpression of NGF Within the Heart of Transgenic Mice Causes Hyperinnervation, Cardiac Enlargement, and Hyperplasia of Ectopic Cells," *Development Biology*, 169:309-321 (1995).

Andrade-Rozental et al., "Characterization of Two Populations of Ectopic Cells Isolated from the Hearts of NGF Transgenic Mice," *Developmental Biology*, 169:533-546 (1995).

Milner et al., Nerve Growth Factor Treatment of Adult Rats Selectively Enhances Innervation of Urinogenital Tract Rather Than Vascular Smooth Muscle, *Int. J. Devl. Neuroscience*, 13(5):393-401 (1995).

Lam et al., "Increased Nerve Growth Factor Inducible-A Gene and C-*FOS* Messenger RNA Levels in the Rat Midbrain and Hindbrain Associated with the Cardiovascular Response to Electrical Stimulation of the Mesencephalic Cuneiform Nucleus," *Neuroscience*, 71(1):193-211 (1996).

Donovan et al., "Identification of an Essential Nonneuronal Function of Neurotrophin 3 in Mammalian Cardiac Development," *Nature Genetics*, 14:210-213 (1996).

Chan et al., "Neurotrophin-4/5 Treatment Reduces Infarct Size in Rats with Middle Cerebral Artery Occlusion," *Neurochemical Research*, 21(7):763-767 (1996).

Abe et al., "Protective Role of Nerve Growth Factor Against Postischemic Dysfunction of Sympathetic Coronary Innervation," *Circulation*, 95:213-220 (1997).

Hempstead et al., "Brain Derived Neurotrophic Factor is Required for the Formation of the Atrial Septum and Coronary Angiogenesis," *Molecular Biology of the Cardiovascular System*, Keystone Symposia, Abstract 119 (1998) (abstract only).

Donovan, "Brain Derived Neurotrophic Factor is an Endothelial Cell Survival Factor Required for Intramyocardial Vessel Stabilization," *Development*, 127:4531-4540 (2000).

Jones et al., "Targeted Disruption of the BDNF Gene Perturbs Brain and Sensory Neuron Development but Not Motor Neuron Development," *Cell*, 76:989-999 (1994).

Ernfors et al., "Mice Lacking Brain-Derived Meurotrophic Factor Develop With Sensory Deficits," *Nature*, 368:147-150 (1994).

Hiltunen et al., "Expression of mRNAs for Neurotrophins and Their Receptors in Developing Rat Heart," *Circ. Res.*, 79:930-939 (1996).

Leibrock et al., "Molecular Cloning and Expression of Brain-Derived Neurotrophic Factor," *Nature*, 341:149-152 (1989).

Rayburn et al., "Histologic Examination of the Placenta in the Growth-Retarded Fetus," *Am. J. Perinatol.*, 6(1):58-61 (1989) (abstract only).

Erickson et al., "Mice Lacking Brain-Derived Neurotrophic Factor Exhibit Visceral Sensory Neuron Losses Distinct from Mice Lacking NT4 and Display a Severe Developmental Deficit in Control of Breathing," *J. Neurosci.*, 16(17):5361-5371 (1996).

Kobayashi et al., "BDNF and NT-4/5 Prevent Atrophy of Rat Rubrospinal Neurons after Cervical Axotomy, Stimulate GAP-43 and Tα1-Tubulin mRNA Expression, and Promote Axonal Regeneration," *J. Neurosci.*, 17(24):9583-9595 (1997).

Ibáñez, "Neurotrophin-4: The Odd One Out in the Neurotrophin Family," *Neurochemical Research*, 21(7):787-793 (1996).

Wang et al., "Localized Synaptic Actions of Neurotrophin-4," *J. Neurosci.*, 18(13):4985-4992 (1998).

Ilag et al., "Pan-Neurotrophin 1: A Genetically Engineered Neurotrophic Factor Displaying Multiple Specificities in Peripheral Neurons In vitro and In vivo," *Proc. Natl. Acad. Sci. USA*, 92(2):607-611 (1995) (abstract only).

Urfer et al., "Specificity Determinants in Neurotrophin-3 and Design of Nerve Growth Factor-Based trkC Agonists by Changing Central Beta-Strand Bundle Residues to Their Neurotrophin-3 Analogs," *Biochemistry*, 36(16):4775-4781 (1997) (abstract only).

Boeshore et al., "TrkB Isoforms with Distinct Neurotrophin Specificities are Expressed in Predominantly Nonoverlapping Populations of Avian Dorsal Root Ganglion Neurons," *J. Neurosci.*, 19(12):4739-4747 (1999).

Chalazonitis, "Neurotrophin-3 as an Essential Signal for the Developing Nervous System," *Molecular Neurobiology*, 12:39-53 (1996).

Binder et al., "Selective Inhibition of Kindling Development by Intraventricular Administration of TrkB Receptor Body,"*J. Neurosci.*, 19(4):1424-1438 (1999) (abstract only).

Zagzag et al., "In Situ Expression of Angiopoletins in Astrocytomas Identifies Angiopoletin-2 as an Early Marker of Tumor Angiogenesis," *Exp. Neurol.*, 159(2):391-400 (1999) (abstract only).

Holash et al., "New Model of Tumor Angiogenesis: Dynamic Balance Between Vessel Regression and Growth Mediated by Angiopoietins and VEGF," *Oncogene*, 18(38):5356-5362 (1999) (abstract only).

Hayes et al., "Angiopoietin-1 and Its Receptor Tie-2 Participate in the Regulation of Capillary-Like Tubule Formation and Survival of Endothelial Cells," *Microvasc. Res.*, 58(3):224-237 (1999) (abstract only).

Segal et al., "Differential Utilization of Trk Autophosphorylation Sites," *J. Biol. Chem.*, 271(33):20175-20181 (1996) (abstract only).

Fandl et al., "Characterization and Crystallization of Recombinant Human Neurotrophin-4," *J. Biol. Chem.*, 269(1):755-759 (1994) (abstract only).

Ibanez et al., "Neurotrophin-4 is a Target-Derived Neurotrophic Factor for Neurons of the Trigeminal Ganglion," *Development*, 117(4):1345-1353 (1993) (abstract only).

Ip et al., "Mammalian Neurotrophin-4: Structure, Chromosomal Localization, Tissue Distribution, and Receptor Specificity," *Proc. Natl. Acad. Sci. USA*, 89(7):3060-3064 (1992) (abstract only).

Hallbook et al., "Evolutionary Studies of the Nerve Growth Factor Family Reveal a Novel Member Abundantly Expressed in Xenopus Ovary," *Neuron*, 6(5):845-858 (1991) (abstract only).

Holash et al., Vessel Cooption, Regression, and Growth in Tumors Mediated by Angiopoietins and VEGF, *Science*, 284:1994-1998 (1999).

Papapetropoulos et al., "Direct Actions of Angiopoietin-1 on Human Endothelium: Evidence for Network Stabilization, Cell Survival, and Interaction with Other Angiogenic Growth Factors," *Laboratory Investigation*, 79(2):213-223 (1999).

Hempstead et al., "Brain Derived Neurotrophic Factor is Required for the Formulation of the Atrial Septum and Coronary Angiogenesis," Weinstein Cardiovascular Development Conference, Vanderbilt University, Nashville, TN, E20 (May 28-30, 1998) (abstract only).

Siemeister et al., "Two Independent Mechanisms Essential for Tumor Angiogenesis: Inhibition of Human Melanoma Xenograft Growth by Interfering with Either the Vascular Endothelial Growth Factor Receptor Pathway or the Tie-2 Pathway," *Cancer Res.*, 59(13):3185-3191 (1999) (abstract only).

Otani et al., "Expressions of Angiopoietins and Tie2 in Human Choroidal Neovascular Membranes," *Invest. Ophthalmol. Vis. Sci.*, 40(9):1912-1920 (1999) (abstract only).

Goede et al., "Analysis of Blood Vessel Maturation Processes During Cyclic Ovarian Angiogenesis," *Lab. Invest.*, 78(11):1385-1394 (1998) (abstract only).

Mack et al., "Biologic Bypass with the Use of Adenovirus-Mediated Gene Transfer of the Complementary Deoxyribonucleic Acid for Vascular Endothelial Growth Factor 121 Improves Myocardial Perfusion and Function in the Ischemic Porcine Heart," *J. Thorac. Cardiovasc. Surg.*, 115(1):168-176 (1998) (abstract only).

Magovern et al., "Direct in vivo Gene Transfer to Canine Myocardium Using a Replication-Deficient Adenovirus Vector," *Ann. Thorac. Surg.*, 62(2):425-433 (1996) (abstract only).

Symes et al., "Gene Therapy with Vascular Endothelial Growth Factor for Inoperable Coronary Artery Disease," *Ann. Thorac. Surg.*, 68(3):830-836 (1999) (abstract only).

Losordo et al., "Gene Therapy for Myocardial Angiogenesis," *Am. Heart J.*, 138(2 Pt. 2):132-141 (1999) (abstract only).

Losordo et al., "Gene Therapy for Myocardial Angiogenesis: Initial Clinical Results with Direct Myocardial Injection of phVEGF165 as Sole Therapy for Myocardial Ischemia," *Circulation*, 98(25):2800-2804 (1996) (abstract only).

Stedman's Medical Dictionary, 27$^{th}$ Edition (reproduced from online version) (2000).

Burgess et al., *J of Cell Bio.* 111:2129-2138 (1990).

Lazar et al., *Molecular and Cell Biology* 8:1247-1252 (1988).

Bowie et al., *Science* 247:1306-1310 (1990).

The Merck Manual of Diagnosis and Therapy, 17th ed., pp. 141, 437-438, 974, 1418, 1654-1655, 1658-1659, 1784-1785 (Mark H. Beers et al. eds., 1999).

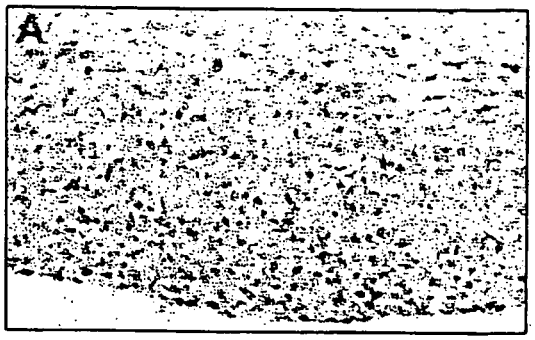
FIG. 4A  FIG. 4B
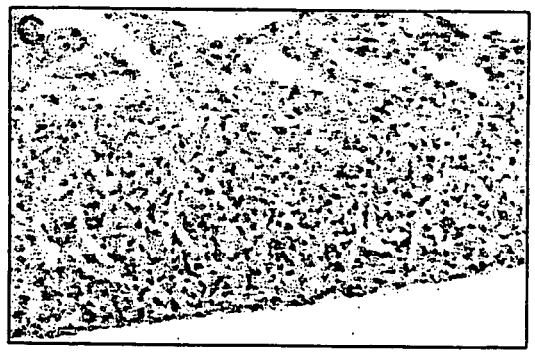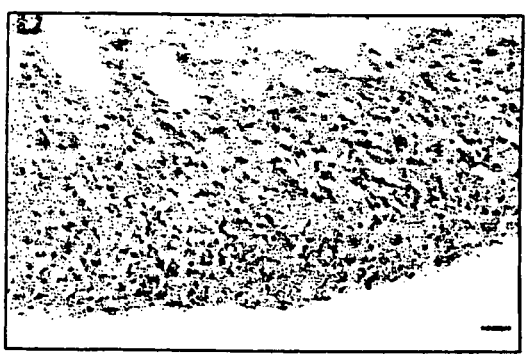
FIG. 4C  FIG. 4D
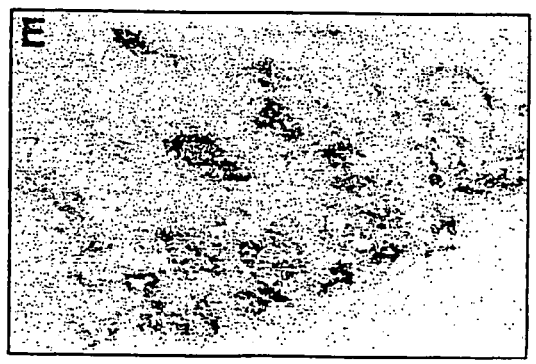
FIG. 4E  FIG. 4F

*FIG. 5A*
*FIG. 5B*
*FIG. 5C*
*FIG. 5D*
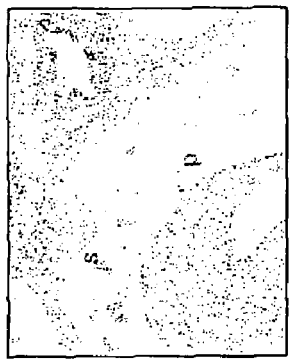
*FIG. 5E*
*FIG. 5F*
*FIG. 5G*
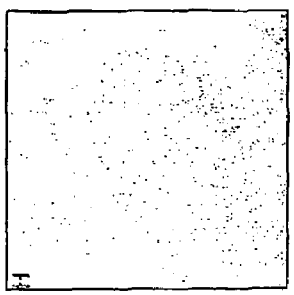
*FIG. 5H*
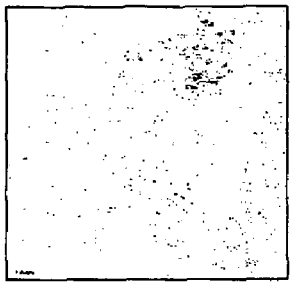
*FIG. 5I*
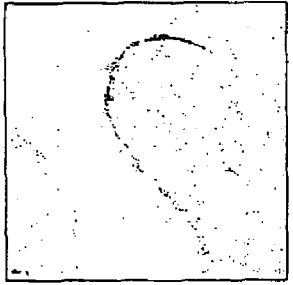
*FIG. 5J*

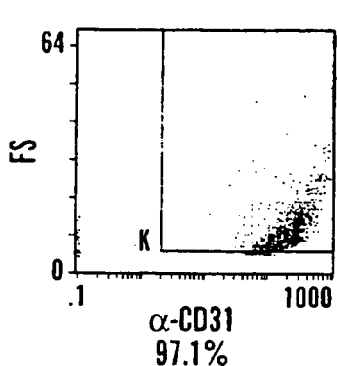
FIG. 6A
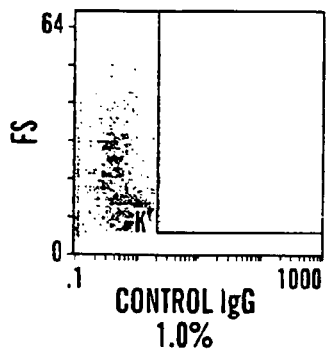
FIG. 6B
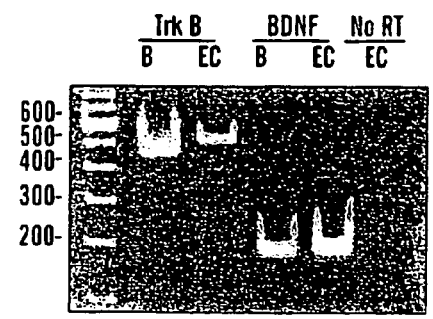
FIG. 6C
10% SERUM
0.6 +/- 0.2%
FIG. 6D
0% SERUM
17.7 +/- 2.1%
FIG. 6E
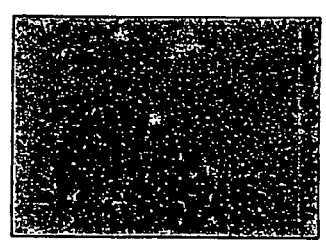
0% SERUM + BDNF
8.4 +/- 1.5%
FIG. 6F
| FLOW CYTOMETRIC ANALYSIS OF ANNEXIN V BINDING | | | | |
|---|---|---|---|---|
| | 10% SERUM | 0% SERUM | 0% SERUM + BDNF | 0% SERUM + VEGF |
| % LIVE | 95.9 | 29.7 | 62.4 | 53.3 |
| % EARLY APOPTOTIC | 1.5 | 46.8 | 22.7 | 15.1 |
| % LATE APOPTOTIC | 2.2 | 22.6 | 12.6 | 22.1 |
FIG. 6G

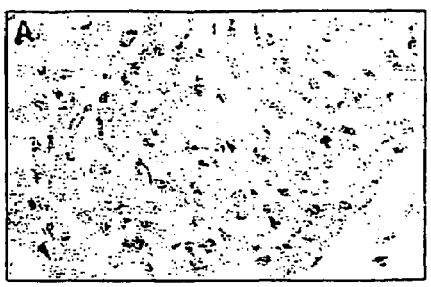
FIG. 7A
FIG. 7B
 
FIG. 7C  FIG. 7D
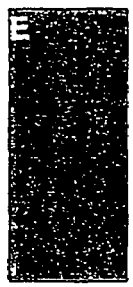 
FIG. 7E  FIG. 7F
FIG. 7G
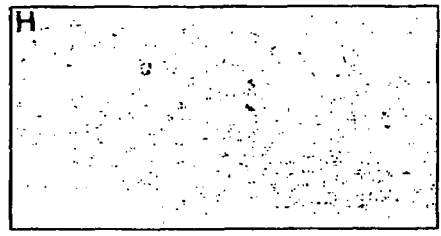
FIG. 7H
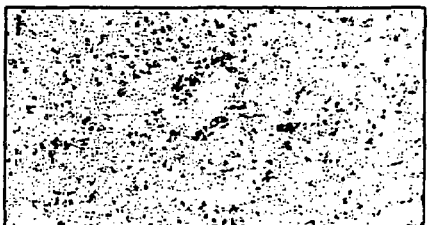
FIG. 7I
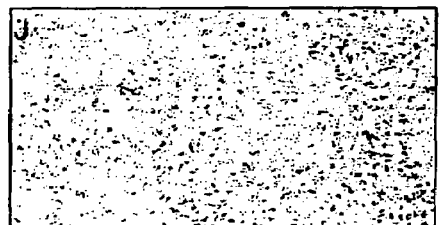
FIG. 7J
FIG. 7K
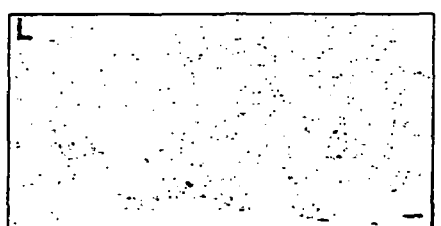
FIG. 7L

FIG. 9A  FIG. 9B
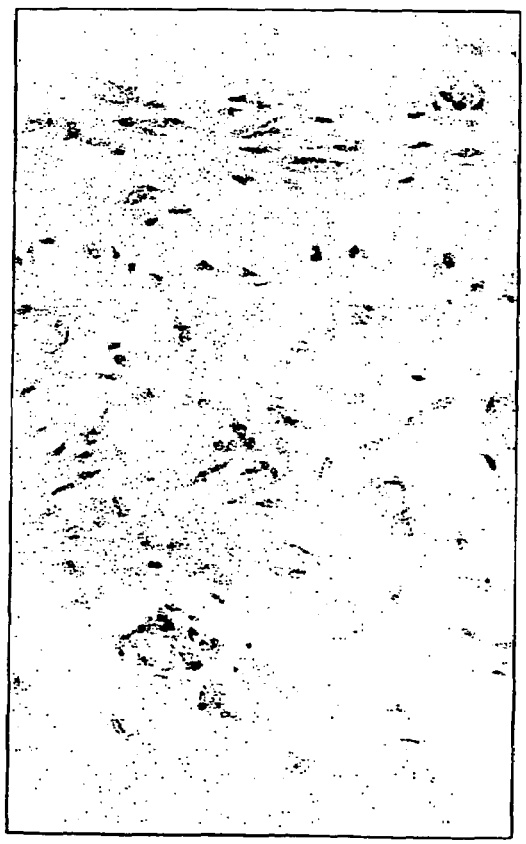
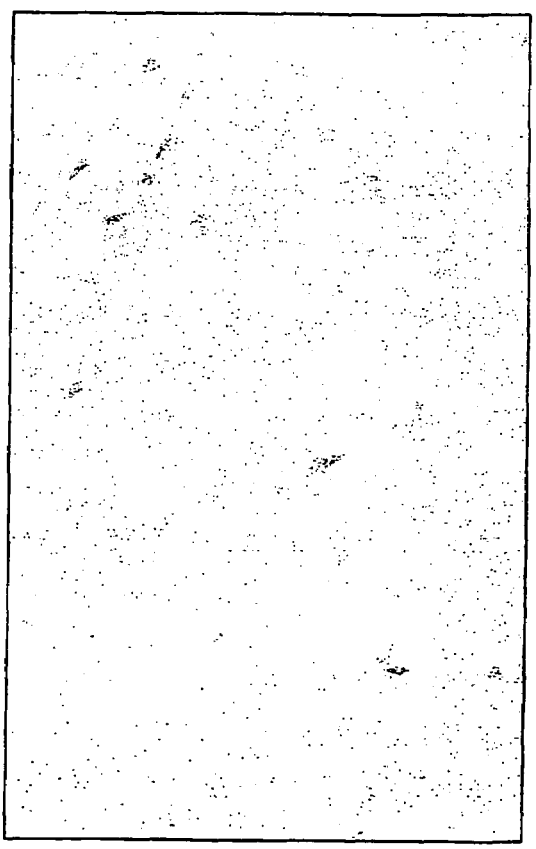
FIG. 9C  FIG. 9D

METHODS FOR INCREASING CAPILLARY DENSITY AND MAINTAINING VIABILITY OF MICROVASCULAR CARDIAC ENDOTHELIAL CELLS USING TRK RECEPTOR LIGANDS

The present application is a continuation of U.S. patent application Ser. No. 09/830,520, filed Jul. 20, 2001 now abandoned, which is a 371 of PCT/US99/25365, filed Oct. 28, 1999, which is hereby incorporated by reference and claims the benefit of U.S. Provisional Patent Application Ser. No. 60/105,928, filed Oct. 28, 1998 and U.S. Provisional Patent Application Ser. No. 60/119,994, filed Feb. 12, 1999.

FIELD OF THE INVENTION

The present invention relates to the use of trk receptor ligands in methods for regulating angiogenesis and vascular integrity, such as methods of inducing angiogenesis, promoting vessel growth or stabilization, treating pathological disorders, inhibiting angiogenesis, and diagnosing or monitoring a pathological disorder. The present invention also relates to a method of screening for a modulator of angiogenesis, vessel growth, or vessel stabilization.

BACKGROUND OF THE INVENTION

Angiogenesis is a precisely regulated process which coordinates the assembly and differentiation of numerous cell types to form the arteries, capillaries and veins of the pre-existing vascular bed. The primitive vasculature is composed of an endothelial plexus, which require the recruitment of pericytes and vascular smooth muscle cells by soluble growth factors secreted by endothelial cells to pattern the vessels into arteries and veins (Risau, "Mechanisms of Angiogenesis," *Nature* 386:671-674 (1997)). In the final steps of vessel formation, the newly formed endothelial cells are stabilized by the extracellular matrix, the formation of a basement membrane and ensheathment with pericytes and smooth muscle cells. Numerous polypeptide growth factors have been implicated in initiating vasculogenesis and angiogenic sprouting, including fibroblast growth factors (bFGF and FGF-2), vascular endothelial growth factor (VEGF), and the angiopoietins (Darland et al., "Blood Vessel Maturation: Vascular Development Comes of Age," *J. Clin. Invest.* 103:167-168 (1999); Ferrara et al., "The Biology of Vascular Endothelial Growth Factor," *Endocrin. Rev.* 18:4-25 (1997)). In addition, platelet derived growth factor B (PDGF-BB), angiopoietin-1 (ang-1), ephrin B2, and TGFβ have been shown to regulate later aspects of the angiogenesis process, in the recruitment of mural cells, and in the patterning of the vascular bed (Yancopoulos et al., "Vasculogenesis, Angiogenesis and Growth Factors: Ephrins Enter the Fray at the Border," *Cell* 93:661-664 (1998); Lindahl et al., "Pericyte Loss and Microaneurysm Formation in the PDGF-B-deficient mice," *Science* 277: 242-245 (1997); Dickman et al., "Defective Haematopoiesis and Vasculogenesis in Transforming Growth Factor Beta 1 Knock Out Mice," *Development* 121:1845-1854 (1995); Yang et al., "Angiogenesis Defects and Mesenchymal Apoptosis in Mice Lacking SMAD5," *Development* 126:1571-1580 (1999)). Very little is known about growth factors which regulate the stabilization and survival of the mature vasculature, although angiopoietin-1 has been proposed as a candidate molecule. Of these factors, only VEGF has been rigorously tested for its ability to initiate angiogenesis in adults in preclinical and clinical trials (Ferrara et al., "The Biology of Vascular Endothelial Growth Factor," *Endocrin. Rev.* 18:4-25 (1997); Mack et al., "Biologic Bypass With the Use of Adenovirus-Mediated Gene Transfer of the Complementary Deoxyribonucleic Acid for Vascular Endothelial Growth Factor 121 Improves Myocardial Perfusion and Function in the Ischemic Porcine Heart," *J. Thoracic and Cardiovascular Surgery* 115:168-176 (1998); Losordo et al., "Gene Therapy for Myocardial Angiogenesis: Initial Clinical Results with Direct Myocardial Injection of phVEGF165 as Sole Therapy for Myocardial Ischemia," *Circulation* 98:2800-2804 (1998)). Although delivery of VEGF by gene transfer can induce an angiogenic response in ischemic tissues, exogenous VEGF induces the formation of fragile, dilated and malformed vessels (Springer et al., "VEGF Gene Delivery to Muscle: Potential Role for Vasculogenesis in Adults," *Molecular Cell* 2:549-558 (1998); Drake et al., "Exogenous Vascular Endothelial Growth Factor Induces Malformed and Hyperfused Vessels During Embryonic Development," *Proc. Natl. Acad. Sci.* 92:7657-7661 (1995)). In addition, recent studies suggest that the endothelial cells of postnatal vessels may become independent of VEGF for their continued survival within several weeks of birth in rodents (Gerber et al., "VEGF is Required for Growth and Survival in Neonatal Mice," *Development* 126:1149-1159 (1999)). Thus, the ultimate endpoint is the definition of the cellular steps and molecular sequences that direct and maintain microvascular assembly leading to therapeutic targets for repair and adaptive remodeling.

In recent studies, the roles of the neurotrophins in regulating cardiovascular development and modulating the vascular response to injury have been investigated (Donovan et al., "Neurotrophin-3 is Required for Mammalian Cardiac Development: Identification of an Essential Nonneuronal Neurotrophin Function," *Nature Genetics* 14:210-213 (1996); Donovan et al., "Neurotrophin and Neurotrophin Receptors in Vascular Smooth Muscle Cells: Regulation of Expression in Response to Injury," *A.J. Path.* 147:309-324 (1995); Kraemer et al., "NGF Activates Similar Intracellular Signaling Pathways in Vascular Smooth Muscle Cells as PDGF-BB But Elicits Different Biological Responses," *Arteriol. Thromb. And Vasc. Biol.* 19:1041-1050 (1999)). The neurotrophins today consist of a family of five related polypeptide growth factors: nerve growth factor (NGF), brain derived neurotrophic factor (BDNF), and neurotrophins 3, 4 (also referred to as neurotrophin 5), and 6 (NT-3, NT-4, NT-6) (Lewin et al., "Physiology of the Neurotrophins," *Ann. Rev. Neuro.* 19:289-317 (1996)). These structurally related proteins mediate their actions on responsive neurons by binding to two classes of cell surface receptor (Lewin et al., "Physiology of the Neurotrophins," *Ann. Rev. Neuro.* 19:289-317 (1996)). The low affinity neurotrophin receptor, p75, binds all neurotrophins and modulates signaling initiated by the second class of neurotrophin receptors, the trk family of receptor tyrosine kinases (what was originally identified as the trk tyrosine kinase receptor is now referred to as trk A, one member of the trk family of receptors). Trk A, trk B, and trk C tyrosine kinases serve as the receptors for NGF, BDNF, and NT-3, respectively, and trk B can also be activated by NT-4.

NT-3 initiates a number of trophic effects on neurons expressing its receptor, trk C, ranging from mitogenesis, promotion of survival, or differentiation, depending on the developmental stage of the target cells (Chalazonitis, "Neurotrophin-3 as an Essential Signal for the Developing Nervous System," *Molecular Neurobiology* 12:29-53 (1996)). The reported sites of action of NT-3 reside primarily in the peripheral nervous system (PNS), various areas of the central nervous system (CNS), and in the enteric nervous system (ENS).

Id. Analyses of the phenotypes of transgenic mice lacking NT-3 or injection of embryos with a blocking antibody have revealed the essential role of NT-3 in development of specific populations of the PNS, and in particular of proprioceptive, nodose, and auditory sensory neurons and of sympathetic neurons. Id. The actions of NT-3 also extend to modulation of transmitter release at several types of synapses in the periphery as well as in the adult CNS. Id.

NT-4 acts via the trk B receptor and supports survival of primary somatic and visceral sensory neurons (Erickson et al., "Mice Lacking Brain-Derived Neurotrophic Factor Exhibit Visceral Sensory Neuron Losses Distinct from Mice Lacking NT4 and Display a Severe Developmental Deficit in Control of Breathing," *J. Neurosci.* 16:5361-5371 (1996)). The major visceral sensory population, the nodose-petrosal ganglion complex (NPG), requires BDNF and NT-4 for survival of a full complement of neurons, however, only one functional NT-4 allele is required to support survival of all NT-4-dependent neurons. Id. NT-4 appears to have the unique requirement of binding to p75 for efficient signaling and retrograde transport in neurons (Ibanez, "Neurotrophin-4: The Odd One out in the Neurotrophin Family," *Neurochemical Research* 21:787-793 (1996)). In addition, while all other neurotrophin knock-outs have proven lethal during early postnatal development, mice deficient in NT-4 have so far only shown minor cellular deficits and develop normally to adulthood.

Trk B receptors and BDNF are highly expressed by central and peripheral neurons, and gene ablation studies have demonstrated the critical role of trk B and BDNF in neuronal differentiation and survival, with gene targeted animals exhibiting abnormalities in cerebellar function and respiratory drive (Lewin et al., "Physiology of the neurotrophins," *Ann. Rev. Neuro.* 19:289-317 (1996); Jones et al., "Targeted Disruption of the BDNF Gene Perturbs Brain and Sensory Neuron Development But Not Motor Neuron Development," *Cell* 76:989-999 (1994); Erickson et al., "Mice Lacking Brain-Derived Neurotrophic Factor Exhibit Visceral Sensory Neuron Losses Distinct From Mice Lacking NT4 and Display a Severe Developmental Deficit in Control of Breathing," *J. Neurosci.* 16:5361-5371 (1996); Schwartz et al., "Abnormal Cerebellar Development and Foliation in the BDNF (−/−) Mice Reveals a Role for Neurotrophins in CNS Patterning," *Neuron* 19:269-281 (1997)).

However, the BDNF:trk B receptor system is expressed at high levels in nonneuronal tissues, including muscle, lung, kidney, heart and the vasculature, where its biological functions are unclear (Donovan et al., "Neurotrophin and Neurotrophin Receptors in Vascular Smooth Muscle Cells: Regulation of Expression in Response to Injury," *A.J. Path.* 147: 309-324 (1995); Timmusk et al., "Widespread and Developmentally Regulated Expression of Neurotrophin-4 mRNA in Rat Brain and Peripheral Tissues," *Eur. J. Neurosci.* 5:605-613 (1993); Hiltunen et al., "Expression of mRNAs for Neurotrophins and Their Receptors in Developing Rat Heart," *Circ. Res.* 79:930-939 (1996); Scarisbrick et al., "Coexpression of the mRNAs for NGF, BDNF and NT-3 in the Cardiovascular System of Pre- and Post-Natal Rat," *J. Neurosci.* 13:875-893 (1993)). Prior studies have identified roles for the related neurotrophin, NT-3, and its receptor, trk C, in regulating cardiac septation and valvulogenesis (Donovan et al., "Neurotrophin-3 is Required for Mammalian Cardiac Development: Identification of an Essential Nonneuronal Neurotrophin Function," *Nature Genetics* 14:210-213 (1996); Tessarollo et al., "Targeted Deletion of all Isoforms of the trk C Gene Suggests the Use of Alternate Receptor by its Ligand Neurotrophin-3 in Neural Development and Implicates trk C in Normal Cardiogenesis," *Proc. Natl. Acad. Sci. USA* 94:14766-014781 (1997). In addition, it has been demonstrated that BDNF and trk B are expressed by vascular smooth muscle cells of the adult aorta, and expression of this ligand:receptor system is upregulated in neointimal cells following vascular injury (Donovan et al., "Neurotrophin-3 is Required for Mammalian Cardiac Development: Identification of an Essential Nonneuronal neurotrophin Function," *Nature Genetics* 14:210-213 (1996)). However, the biological actions of BDNF and related neurotrophins in cardiovascular function and development have not been assessed.

The present invention is directed to functions of the neurotrophins and the trk receptor family related to vascular biology.

SUMMARY OF THE INVENTION

The present invention relates to a method of inducing angiogenesis which includes delivering a trk receptor ligand in an amount effective to induce angiogenesis.

The present invention also relates to a method for treating a pathological disorder in a patient which includes administering a trk receptor ligand in an amount effective to treat the pathological disorder by inducing angiogenesis.

Another aspect of the present invention is a method of promoting vessel growth or stabilization which includes delivering a trk receptor ligand in an amount effective to promote vessel growth or stabilization.

Yet another aspect of the present invention is a method for treating a pathological disorder in a patient which includes administering a trk receptor ligand in an amount effective to treat the pathological disorder by promoting vessel growth or stabilization.

The present invention also relates to a method of inhibiting angiogenesis which includes delivering an inhibitor of expression or activity of a trk receptor ligand in an amount effective to inhibit angiogenesis.

The present invention also relates to a method for treating a pathological disorder in a patient which includes administering an inhibitor of expression or activity of a trk receptor ligand in an amount effective to treat the pathological disorder by inhibiting angiogenesis.

The present invention further relates to a method of screening for a modulator of angiogenesis, vessel growth, or vessel stabilization including providing a candidate compound and detecting modulation of a trk receptor ligand induced signal transduction pathway in a cell in the presence of the candidate compound, wherein modulation of the signal transduction pathway indicates that the candidate compound is a modulator of angiogenesis, vessel growth, or vessel stabilization.

Another aspect of the present invention is a method of diagnosing or monitoring a pathological disorder in a patient which includes determining the presence or amount of a trk receptor ligand or activation of a trk receptor ligand in a biological sample.

Although several growth factors have been identified as playing roles in the initiation of angiogenesis, most notably VEGF, the present invention shows that trk receptor ligands, e.g., trk B and trk C ligands, have unique functions in vascular biology, including induction of angiogenesis, vessel growth, and vessel stabilization. Unlike VEGF and VEGF receptors, which are expressed at high levels during embryogenesis but are expressed at only low levels during adulthood, expression of the trk B and trk C ligands by the vasculature is initiated during late gestation, and expression increases with postnatal life into adulthood. These distinctive patterns of expression suggest that endothelial cells may not require continued exposure to VEGF during adulthood, a point recently confirmed in animal models (Gerber et al., "VEGF is Required for Growth and Survival in Neonatal Mice," *Development* 126:1149-1159 (1999), which is hereby incorporated by reference).

The in vitro and in vivo studies of the present invention support a survival role for the trk B and trk C ligands, as opposed to the well characterized mitogenic effects of VEGF on endothelial cells. As such, the trk B and trk C ligands demonstrate a critical stabilizing function for the vasculature, in preventing endothelial cell apoptosis. It is also important to recognize the delivery of other angiogenic factors, like VEGF, at high levels has been accompanied by significant adverse effects, with enhanced vessel fragility and the local induction of hemangiomas, effects which might reflect the known mitogenic and permeability promoting effects of VEGF (Drake et al., "Exogenous Vascular Endothelial Growth Factor Induced Malformed and Hyperfused Vessels During Embryonic Development," *Proc. Natl. Acad. Sci. USA* 92:7657-7661 (1995); Springer et al., "VEGF Gene Delivery to Muscle: Potential Role for Vasculogenesis in Adults," *Molecular Cell* 2:549-558 (1998), which are hereby incorporated by reference). In contrast, overexpression of a trk receptor ligand in the developing heart results in an increased capillary network, but no evidence of vascular fragility or altered vessel permeability.

The actions of the trk receptor ligands also are distinguishable from those reported for the angiopoietins. Angiopoietins play a role in angiogenesis by conveying signals that stabilize the endothelial cells within newly formed blood vessels. In vitro studies suggest that angiopoietin-1 may act as a survival factor for endothelial cells (Hayes et al., "Angiopoietin-1 and Its Receptor Tie-2 Participate in the Regulation of Capillary-Like Tubule Formation and Survival of Endothelial Cells," *Microvasc. Res.* 58:224-237 (1999), which is hereby incorporated by reference). As such, angiopoietin-1 is widely expressed by the smooth muscle cells surrounding endothelial cells, which express the angiopoietin-1 receptor, Tie2. Thus, unlike the trk receptor ligands which can act in an autocrine manner to support endothelial cell survival, angiopoietin-1 is produced by smooth muscle cells and acts in a paracrine manner to promote endothelial cell survival. Although both angiopoietin-1 and the trk receptor ligands are expressed by cells of the postnatal and adult vasculature, the phenotype of BDNF null mutant and angiopoietin-1 or Tie2 null mutant animals is distinctive. There are also important differences in the ability of trk receptor ligands and the angiopoietins to initiate angiogenesis in in vivo models. In most in vivo studies when angiopoietin-1 alone has been injected locally or systemically into mice. Results have shown marginal changes in angiogenesis. In contrast, trk receptor ligands BDNF, NT-3 and NT-4 appear to be similarly effective as VEGF in promoting the development of vascular networks.

BRIEF DESCRIPTION OF THE DRAWINGS

FIGS. 4A-F show intramyocardial hemorrhage and vascularization in BDNF (−/−) embryos. E16.5 embryos (panels A and B) and E17.5 embryos (panels C, D, E, and F) were harvested from BDNF (+/−) females, and sections of the developing heart were analyzed histologically following hematoxylin and eosin staining. Panels E and F show immunohistochemical analysis of intramyocardial vessels using an anti-CD31 antisera to detect endothelial cells within arterioles, venules, and capillaries of the ventricular wall. Panels A, C, and E are BDNF (+/+) animals. Panels B, D, and F are BDNF (−/−) animals. Bars, 40 μm (panels A, B, C, and D); 20 μm (panels E and F).

FIGS. 5A-J show atrial septal formation in BDNF (+/+) and (−/−) embryos through histological and immunohistochemical analyses of atrial septal formation in BDNF animals at E11.5 (panels A and D), E14.5 (panels B and E), E16.5 (panels C and F), and P0 (panels G and H). Sections of the atrial septum were stained with hematoxylin and eosin in BDNF (+/+) animals (panels A, B, and C) and BDNF (−/−) animals (panels D, E, and F). p=septum primum; s=septum secundum. Panels G, H, I, and J show the use of immunohistochemical analysis to detect CD31 (panel H), BDNF (panel I), and kinase active trk B (panel J) to assess expression in the region of the atrial septum of E18.5 BDNF (+/+) embryos. Preincubation of trk B specific antisera with the immunizing peptide confirms antisera specificity on sections from E18.5 BDNF (+/+) embryos (panel G). Bars, 40 μm (panels A-F); 20 μm (panels G-J).

FIGS. 6A-G show that BDNF supports the survival of cardiac microvascular endothelial cells. Panels A and B show flow cytometric analysis of cardiac microvascular endothelial cells incubated with anti-CD31 antisera (panel A) or control IgG (panel B). 97% of cells exhibit CD31 reactivity and 1% react with control IgG. Panel C shows RT-PCR analysis of transcripts for BDNF and kinase active trk B mRNA in cardiac microvascular endothelial cells ("ECs") and adult murine brain (B). Amplification of BDNF (360 bp) and the regions of the kinase domain of trk B (571 bp) are detectable in cardiac endothelial cells and adult brain samples. To ensure the absence of DNA contamination, RNA samples were amplified using primers without the reverse transcription step and these reactions yielded no products (no RT). Panels D, E, and F show TUNEL analysis of microvascular endothelial cells. ECs were cultured in media containing 10% serum (panel D), or in media containing 0% serum (panels E and F) in the presence of BDNF (100 ng/ml) (panel F) for 48 hours. 1500 cells per sample were analyzed and the mean and standard deviation of four samples is indicated. Results are representative of two experiments performed in quadruplicate on cultures from different litters of animals (Magnification: 20×). Panel G shows flow cytometric analysis of annexin V binding. Cardiac microvascular endothelial cells were cultured in the indicated conditions in the presence of BDNF (25 ng/ml) or VEGF (10 ng/ml) for 48 hours prior to incubation with FITC-annexin V and propidium iodide for flow cytometry of $1\times10^4$ cells per condition. Results are representative of two independent experiments performed on cultures from different litters of animals.

FIGS. 7A-L show that overexpression of BDNF in gestational hearts results in increased capillary density through the analysis of Nes-BDNF hearts from E18.5 embryos (panels A, C, D, G, I, and K) or wildtype littermates (panels B, E, F, H, J, and L). Panels A and B show that histologic analysis reveals abnormal vascularity of Nes-BDNF ventricular wall. Panels C, D, E, and F show that immunofluorescence detection of BDNF demonstrates increased expression of Nes-BDNF (panel F) as compared with wildtype littermates (panel D). Preincubation of the BDNF antisera with the immunizing peptide prior to immunofluorescence (panels C and E) confirms the specificity of the antisera. Immunofluorescence on paired samples was performed in parallel, using FITC-conjugated secondary antisera and imaged by optical sectioning at identical settings. Results are representative of those observed with three transgenic and three wildtype embryos. Panels E and F show that CD31 immunoreactivity reveals an enhanced vessel density in Nes-BDNF embryos as compared to wildtype littermates. Immunoreactivity was detected using a VIP substrate (red reaction product). Tissue sections are representative of those analyzed in four transgenic and four wildtype littermates. Panels G and H show that α-actinin immunoreactivity, to detect vascular smooth muscle cells, is similar in Nes-BDNF transgenic and wild-type hearts. Note positivity of the large vessel in the wildtype section, but absence of reactivity of capillaries in wildtype and Nes-BDNF embryos. Panels I and J show PCNA immunoreactivity in sections of wildtype and Nes-BDNF embryonic hearts. Panels G-H show results that are representative of those analyzed in four transgenic and four wildtype littermates. Bars, 15 µm (panels A and B); 100 µm (panels C-F); 40 µm (panels G-L).

FIGS. 9A-D show histological analysis of Matrigel sections containing the indicated growth factor (at 50 ng/ml) or no additional growth factor (control). Following paraformaldehyde fixation, paraffin embedded tissue was sectional at 10 microns, and processed with hematoxylin and eosin staining. A minimum of 7 mm of tissue was analyzed in serial section analysis and representative sections were photographed at the indicated magnifications (left panels: 40×; right panels: 160×).

DETAILED DESCRIPTION OF THE INVENTION

Figure 1A:
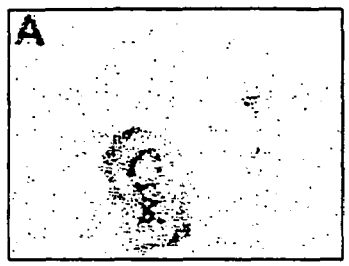
FIGS. 1A-J show the expression of neurotrophins in adult and embryonic rodent hearts. In particular, these figures show immunohistochemical detection of BDNF (panels A, and D), NT-3 (panel B), NT-4 (panel C), or kinase active trk B (panel E) in rodent hearts. Panels A, B, and C show sections of the left ventricular wall of adult female rats (6 weeks). Comparable results were obtained with adult mouse heart sections. Panels D and E show sections of the ventricular wall of BDNF (+/+) mouse embryos at E18.5. Panel F shows heart sections from a BDNF (+/+) E18.5 embryo incubated with anti-BDNF antisera to document antisera specificity. In panels A-F, VIP-based immunodetection was utilized, yielding a red reaction product. Panels G, H, I, and J show double immunofluorescence detection of PECAM (CD31) reactivity (using a rhodamine-conjugated primary antibody) and either BDNF reactivity (panels G and I) or kinase active trk B reactivity (using FITC conjugated secondary antibody) (panels H and I), with sections of adult mouse hearts (panels G and H) or E18.5 mouse hearts (panels I and J). Bars, 50 μm (panels A, B, and C); 25 μm (panels D, E, and F); 30 μm (panels G, H, I, and J).

The present invention relates to a method of inducing angiogenesis which includes delivering a trk receptor ligand in an amount effective to induce angiogenesis.

In a preferred embodiment, the trk receptor ligand is a trk B receptor ligand.

In another preferred embodiment, the trk receptor ligand is a trk C receptor ligand.

As used herein, trk ligands include proteins or polypeptides and fragments thereof, including the native neurotrophins and mutants thereof, small chemical molecules, recombinant molecules, and chimeric molecules which interact with and activate trk receptors. Chimeric trk receptor ligands include mutagenized neurotrophins which are capable of activating more than one trk receptor (see, e.g., Urfer et al., "Specificity Determinants in Neurotrophin-3 and Design of Nerve Growth Factor-Based trkC Agonists by Changing Central Beta-Strand Bundle Residues to Their Neurotrophin-3 Analogs," *Biochemistry* 36:4775-4781 (1997); Ilag et al., "Pan-Neurotrophin 1: A Genetically Engineered Neurotrophic Factor Displaying Multiple Specificities in Peripheral Neurons in vitro and in vivo," *Proc. Natl. Acad. Sci. USA* 92:607-611 (1995), which are hereby incorporated by reference).

Suitable trk receptor ligands include brain derived neurotrophic factor ("BDNF"), NT-3, NT-4, and recombinant and small molecule mimics thereof.

BDNF is a neurotrophin best characterized for its survival and differentiative effects on neurons expressing the trk B receptor kinase. Deficient expression of BDNF does not affect the assembly or patterning of endothelial cells in intramyocardial vessels, but impairs their survival. BDNF deficiency induces endothelial cell apoptosis, leading to intraventricular wall hemorrhage, depressed cardiac contractility, and early postnatal death. In contrast, ectopic BDNF overexpression is associated with increased capillary density and increased survival of cardiac microvascular endothelial cells. Thus, expression of BDNF is required for the stabilization of intramyocardial vessels during late embryogenesis, through direct actions on endothelial cells.

NT-3 is a member of the neurotrophin family and exhibits significant homology with NGF and BDNF (Hohn et al., "Identification and Characterization of a Novel Member of the Nerve Growth Factor/Brain-Derived Neurotrophic Factor Family," *Nature* 334:339-341 (1990), which is hereby incorporated by reference). NT-3 mediates its actions on trk C expressing neurons, and its role in promoting the survival of subclasses of sensory and sympathetic neurons during the development of the peripheral nervous system has been established through the analysis of gene targeted mice (Snider, "Functions of the Neurotrophins During Nervous System Development: What the Knockouts are Teaching Us," *Cell* 77:627-638 (1994), which is hereby incorporated by reference). NT-3 is highly expressed by capillaries in adult rodent heart (see FIG. 1). In addition, NT-3 promotes angiogenesis in a Matrigel assay (see Example 14, below).

NT-4 is the most divergent member of the neurotrophins and, in contrast with other neurotrophins, its expression is ubiquitous and less influenced by environmental signals (Ibanez, "Neurotrophin-4: The Odd One Out in the Neurotrophin Family," *Neurochemical Research,* 21:787-793 (1996), which is hereby incorporated by reference). It shares its two receptors (trkB and p75) with other members of the neurotrophin family, e.g., BDNF. Id. Evidence suggests that the level of NT-4 mRNA in skeletal muscle is controlled by muscle activity and that muscle derived NT-4 is an activity dependent neurotrophic signal for growth and remodeling of adult motor neuron innervation, and may thus be partly responsible for the effects of exercise and electrical stimulation on neuromuscular performance. Id. NT-4 mRNA is expressed at significant levels in the embryonic heart, but falls to undetectable levels in the adult heart (Timmusk et al., "Widespread and Developmentally Regulated Expression of Neurotrophin-4 mRNA in Rat Brain and Peripheral Tissues," *Eur. J. Neurosci.* 5:605-613 (1993), which is hereby incorporated by reference). However, NT-4 is as potent as VEGF in promoting the formation of vascular networks in an in vivo Matrigel assay (see Example 14, below).

The trk receptor ligand may be employed in accordance with the present invention by administering a protein or polypeptide ligand.

The trk receptor ligand may also be employed in accordance with the present invention by expression of such trk receptor ligand in vivo, which is often referred to as "gene therapy."

The genes encoding the trk receptor ligand and proteins or polypeptides derived therefrom are known in the art, as well as methods for producing such proteins or polypeptides, e.g., recombinantly (U.S. Pat. No. 5,180,820 to Barde et al.; U.S. Pat. No. 5,229,500 to Barde et al.; U.S. Pat. No. 5,438,121 to Barde et al.; U.S. Pat. No. 5,453,361 to Yancopoulos et al.; U.S. Pat. No. 5,770,577 to Kinstler et al.; U.S. Pat. No. 5,235,043 to Collins et al.; Enfors et al., "Molecular Cloning and Neurotrophic Activities of a Protein with Structural Similarities to Nerve Growth Factor: Developmental and Topographical Expression in the Brain," *Proc. Natl. Acad. Sci. USA* 87:5454-5458 (1990); Hohn et al., "Identification and Characterization of a Novel Member of the Nerve Growth Factor/Brain-Derived Neurotrophic Family," *Nature* 344:339-341 (1990); Jones et al., Molecular Cloning of a Human Gene that is a Member of the Nerve Growth Factor Family," *Proc. Natl. Acad. Sci. USA* 87:8060-8064 (1990); Maisonpierre et al., "Neurotrophin-3: A Neurotrophic Factor Related to NGF and BDNF," *Science* 24:1446-1451 (1990); and Rosenthal et al., "Primary Structure and Biological Activity of a Novel Human Neurotrophic Factor," *Neuron* 4:767-773 (1990); Fandl et al., "Characterization and Crystallization of Recombinant Human Neurotrophin-4," *J. Biol. Chem.* 269:755-759 (1994); Ibanez et al., "Neurotrophin-4 is a Target-Derived Neurotrophic Factor For Neurons of the Trigeminal Ganglion," *Development* 117:1345-1353 (1993); Ip et al., "Mammalian Neurotrophin-4: Structure, Chromosomal Localization, Tissue Distribution, and Receptor Specificity," *Proc. Natl. Acad, Sci. USA* 89:3060-3064 (1992); Hallbrook et al., "Evolutionary Studies of the Nerve Growth Factor Family Reveal A Novel Member Abundantly Expressed in Xenopus Ovary," *Neuron* 6:845-858 (1991), which are hereby incorporated by reference).

Cells may be engineered by procedures known in the art, including by use of a retroviral particle containing RNA encoding the trk receptor ligand of the present invention. Similarly, cells may be engineered in vivo for expression of trk receptor ligand in vivo by procedures known in the art. As known in the art, for example, a producer cell comprising a retroviral particle containing RNA encoding the trk receptor ligand of the present invention may be administered to a patient for expression of the trk receptor ligand in vivo. These and other methods for administering the trk receptor ligand of the present invention should be apparent to those skilled in the art from the teachings of the present invention.

Construction of appropriate expression vehicles and vectors for gene therapy applications will depend on the organ to be treated and the purpose of the gene therapy. The selection of appropriate promoters and other regulatory DNA will proceed according to known principles, based on a variety of known gene therapy techniques. For example, retroviral mediated gene transfer is a very effective method for gene therapy, as systems utilizing packaging defective viruses allow the production of recombinants which are infectious only once, thus avoiding the introduction of wild-type virus into an organism. Alternative methodologies for gene therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

Viral vectors which may be used to produce stable integration of genetic information into the host cell genome include adenoviruses, the adenoassociated virus vectors (AAV) (Flotte et al., *Gene Ther.,* 2:29-37 (1995); Zeitlin et al., *Gene Ther.,* 2:623-31 (1995); Baudard et al., *Hum. Gene Ther.,* 7:1309-22 (1996); which are hereby incorporated by reference), and retroviruses. For a review of retrovirus vectors, see Austin, *Gene Ther.,* 1(Suppl 1):S6-9 (1994) and Eglitis, *Blood,* 71:717-22 (1988), which are hereby incorporated by reference. Other viral vectors are derived from herpesviruses, etc.

Retroviruses are RNA viruses which are useful for stably incorporating genetic information into the host cell genome. When they infect cells, their RNA genomes are converted to a DNA form (by the viral enzyme reverse transcriptase). The viral DNA is efficiently integrated into the host genome, where it permanently resides, replicating along with host DNA at each cell division. This integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely.

Retroviruses are therefore attractive vectors, because they can permanently express a foreign gene in cells. Moreover, they can infect virtually every type of mammalian cell, making them exceptionally versatile. In the design and use of retroviral vectors, the vectors usually contain a selectable marker as well as the foreign gene to be expressed. Most of the viral structural genes are gone, so these vectors cannot replicate as viruses on their own. To prepare virus stocks, cloned proviral DNA is transfected into a packaging cell. These cells usually contain an integrated provirus with all its genes intact, but lacking the sequence recognized by the packaging apparatus. Thus, the packaging provirus produces all the proteins required for packaging of viral RNA into infectious virus particles but it cannot package its own RNA. The packaging system may allow use of a variety of viral envelopes to alter viral tropism, and ability to infect human cells. Examples include retroviral vectors using amphotropic, HIV-1/2, SIV, Gibbon Ape Leukemia Virus ("GALV"), or Vesicular Stomatis Virus ("VSV") envelope. Vector packaging systems and/or backbones may be derived from various sources such as MoMuLV, or even lentiviruses such as HIV-1, SIV, etc. RNA transcribed from the transfected vector is packaged into infectious virus particles and released from the cell. The resulting virus stock is termed helper-free, because it lacks wild-type replication-competent virus. This virus stock can be used to infect a target cell culture. The recombinant genome is efficiently introduced, reverse-transcribed into DNA (by reverse transcriptase deposited in the virus by the packaging cells), and integrated into the genome. Thus, the cells now express the new virally introduced gene, but they never produce any virus, because the recombinant virus genome lacks the necessary viral genes.

The invention, therefore, provides for the expression of trk receptor ligands in vivo by methods including viral vectors which carry the nucleic acids encoding the trk receptor ligand.

Preferably, the trk receptor ligand is delivered in an assay system, sample, or target organ.

For inducing angiogenesis and promoting vascular survival, delivering an effective amount of a trk receptor ligand includes delivering nanomolar concentrations of ligand to the target site, as described for administration of VEGF (see, e.g., Mack et al., "Biologic Bypass With the Use of Adenovirus-Mediated Gene Transfer of the Complementary Deoxyribonucleic Acid for Vascular Endothelial Growth Factor 121 Improves Myocardial Perfusion and Function in the Ischemic Porcine Heart," *J. Thorac. Cardiovasc. Surg.* 115:168-176 (1998); Magovern et al., "Direct in vivo gene Transfer to Canine Myocarium Using a Replication-Deficient Adenovirus Vector," *Ann. Thorac. Surg* 62:425-433 (1996); Symes et al., "Gene Therapy with Vascular Endothelial Growth Factor for Inoperable Coronary Artery Disease," *Ann. Thorac. Surg.* 68:830-836 (1999); Losordo et al., "Gene Therapy for Myocardial Angiogenesis," *Am. Heart J.* 138(2, Pt. 2):132-141 (1999); Losordo et al., "Gene Therapy for Myocardial Angiogenesis: Initial Clinical Results With Direct Myocardial Injection of phVEGF165 as Sole Therapy for Myocardial Ischemia," *Circulation* 98:2800-2804 (1998), which are hereby incorporated by reference). For gene delivery, an effective amount is sufficient quantities of the vector to ensure synthesis of nanomolar concentrations of protein or polypeptide ligand in the target site.

In accordance with the method of the present invention, the trk receptor ligand can be administered in vivo orally, intravenously, intramuscularly, intraperitoneally, subcutaneously, by intranasal instillation, by application to mucous membranes, such as, that of the nose, throat, and bronchial tubes, intracerebrally, into cerebral spinal fluid, or by instillation into hollow organ walls or newly vascularized blood vessels. It may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the trk receptor ligand of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The trk receptor ligand of the present invention may also be administered in injectable dosages by solution or suspension of the trk receptor ligand in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the trk receptor ligand of the present invention in solution or suspension may be packaged in a pressurized aerosol container together with suitable propellants, for example, hydrocarbon propellants like propane, butane, or isobutane with conventional adjuvants. The trk receptor ligand of the present invention also may be administered in a non-pressurized form such as in a nebulizer or atomizer.

The present invention also relates to a method for treating a pathological disorder in a patient which includes administering a trk receptor ligand in an amount effective to treat the pathological disorder by inducing angiogenesis in the manner described above.

In one embodiment, the pathological disorder is cardiac ischemia. Cardiac ischemia includes cerebrovascular disorders caused by insufficient cerebral circulation. Thrombi or emboli due to atherosclerotic or other disorders (e.g., arteritis or rheumatic heart disease) commonly cause ischemic arterial obstruction.

In another embodiment, the pathological disorder is a non-cardiac vascular disorder including atherosclerosis, renal vascular disease, and stroke.

In yet another embodiment, the pathological disorder is a wound. Such wounds include, but are not limited to, chronic stasis ulcers, diabetic complications, complications of sickle cell disease, thallasemia and other disorders of hemoglobin, and post-surgical wounds.

In a further embodiment, the pathological disorder is a condition of placental insufficiency. Such conditions include, but are not limited to, intrauterine growth retardation.

In yet a further embodiment, the pathological disorder unvascularized tissue related to grafts and transplants (see, e.g., PCT International Application No, WO 99/06073 to Isner, which is hereby incorporated by reference).

Another aspect of the present invention is a method of promoting vessel growth or stabilization which includes delivering an effective amount of a trk receptor ligand in an amount effective to promote vessel growth or stabilization in the manner described above.

Yet another aspect of the present invention is a method for treating a pathological disorder in a patient which includes administering a trk receptor ligand in an amount effective to treat the pathological disorder by promoting vessel growth or stabilization in the manner described above.

In a preferred embodiment, the pathological disorder relates to endothelial cell apoptosis or necrosis. An example of such a pathological disorder is vasculitis.

The present invention also relates to a method of inhibiting angiogenesis which includes delivering an inhibitor of expression or activity of a trk receptor ligand in an amount effective to inhibit angiogenesis.

Suitable inhibitors include any component capable of blocking the binding of ligands to the receptor, thus inhibiting receptor activation.

In one embodiment, the delivering includes delivering a nucleic acid sequence encoding an antisense molecule complementary to mRNA encoding a trk receptor ligand as is known in the art (antisense includes ribozymes).

In another embodiment, the delivering includes delivering a receptor body (Binder et al., "Selective Inhibition of Kindling Development by Intraventricular Administration of TrkB Receptor Body," *J. Neurosci.* 19:1424-1436 (1999), which is hereby incorporated by reference). Receptor bodies include the extracellular domain of the receptor and may be bound to the Fc portion of an immunoglobulin molecule for delivery. Delivery of receptor bodies can be used to bind native trk receptor ligand and thus prevent the activation of trk receptors.

For inhibition of angiogenesis, delivering an effective amount of an inhibitor of expression or activity of a trk receptor ligand includes delivering sufficient inhibitor to inhibit nanomolar concentrations of the native ligand(s) in the target organ.

The present invention also relates to a method for treating a pathological disorder in a patient which includes administering an inhibitor of expression or activity of a trk receptor ligand in an amount effective to treat the pathological disorder by inhibiting angiogenesis.

In one embodiment, the pathological disorder is a vascular proliferative disease. Suitable vascular proliferative diseases include hemangiomas and proliferative retinopathy.

In another embodiment, the pathological disorder is cancer.

The present invention further relates to a method of screening for a modulator of angiogenesis, vessel growth, or vessel stabilization. This method includes providing a candidate compound and detecting modulation of a trk receptor ligand induced signal transduction pathway in a cell in the presence of the candidate compound, wherein modulation of the signal transduction pathway indicates that the candidate compound is a modulator of angiogenesis, vessel growth, or vessel stabilization.

In a preferred embodiment, the detecting comprises assessing trk tyrosine phosphorylation. In particular, trk receptor activation can be assessed through the use of antibodies which specifically recognize tyrosine-phosphorylated epitopes in the cytoplasmic domain of activated trk receptors (Segal et al., "Differential Utilization of Trk Autophosphorylation Sites," *J. Biol. Chem.* 271:20175-20181 (1996), which is hereby incorporated by reference). As trk receptors become tyrosine phosphorylated following the binding of ligand, these reagents can be used to detect activated, but not inactive, trk receptors. Commercial sources of these reagents include Santa Cruz Biotechnologies, Santa Cruz, Calif.

Another aspect of the present invention is a method of diagnosing or monitoring a pathological disorder in a patient which includes determining the presence or amount of a trk receptor ligand or activation of a trk receptor ligand in a biological sample.

Suitable pathological disorders include cardiac ischemia, atherosclerosis, renal vascular disease, stroke, a wound, placental insufficiency, unvascularized tissue related to grafts and transplants, disorders relating to endothelial cell apoptosis or necrosis, hemangiomas, proliferative retinopathy, and cancer.

In a preferred embodiment, the presence or amount of trk receptor ligands in certain tissue, e.g., tumor cells, sclerotic vessels, and vascular channels surrounded by tumor cells, may be used as an early maker of tumor angiogenesis (Zagzag et al., "In Situ Expression of Angiopoietins in Astrocytomas Identifies Angiopoietin-2 as an Early Marker of Tumor Angiogenesis," *Exp. Neurol.* 159:391-400 (1999), which is hereby incorporated by reference).

Determining the presence or amount of a trk receptor ligand or activation of a trk receptor ligand in a biological sample may be accomplished using methods known to those of ordinary skill in the art. In one embodiment, the determining comprises assessing trk tyrosine phosphorylation, as described above.

Suitable biological samples include blood, urine, hair, cheek scrapings, semen, tissue biopsy, and saliva.

EXAMPLES

Example 1

BDNF Mutant Mice

Heterozygous (+/−) BDNF mice (Ernfors et al., "Mice Lacking Brain-Derived Neurotrophic Factor Develop with Sensory Defects," *Nature,* 368:147-150 (1994), which is hereby incorporated by reference), (STOCK BDNF$^{tm1Jae}$ and C5713L/6J backcrossed BDNF$^{tm1Jae}$) were obtained from Jackson Laboratories (Bar Harbor, Me.), and were intercrossed by brother/sister matings for embryo analysis. The morning of the detection of a vaginal plug was considered day 0.5, and the gestational age was assigned. At the time of embryo harvest, morphologic criteria were used in assigning developmental age. Key criteria included limb bud, eye and ear development, crown-rump length and weight (Kaufman, "The Atlas of Mouse Development," Academic Press, Inc. San Diego (1992), which is hereby incorporated by reference). The genotype of each embryo or newborn mouse was determined by analysis of head derived DNA using PCR amplification with primer sequences as described in Ernfors et al., "Mice Lacking Brain-Derived Neurotrophic Factor Develop with Sensory Deficits," *Nature* 368:147-150 (1994), which is hereby incorporated by reference.

Mice were sacrificed and bodies fixed immediately in 3% paraformaldehyde in phosphate buffered saline for 18 hours, and the contents of the thoracic cavity were dissected en bloc. Tissues were embedded in paraffin for histologic analysis. Tissues used for immunohistochemistry were infiltrated with 30% sucrose prior to cryoprotection in 30% sucrose/OCT. The bodies of embryos of gestational age of E14.5 or less were embedded without prior dissection. Sections of 10 microns were stained using hematoxylin and eosin as described in Donovan et al., "Neurotrophin-3 is Required for Mammalian Cardiac Development Identification of an Essential Nonneuronal Neurotrophin Function," *Nature Genetics* 14:210-213 (1996), which is hereby incorporated by reference). For electron microscopic analysis, the hearts were immediately removed from newborn mice sacrificed by decapitation, and fixed in Karnovsky's fixative (2% glutaraldehyde/paraformaldehyde in cacodylate buffer) for 18 hours prior to embedding in Epon. Tissues were sectioned at 1 micron and stained with toluidine blue for initial evaluation and then ultrathin sections were cut with a diamond knife, counterstained with lead citrate, and viewed with an electron microscope.

Example 2

Immunohistochemical Analysis

Monoclonal antisera specific for α-actinin 1E12 (undiluted monoclonal supernatant) was utilized for detection of vascular smooth muscle cells. Biotinylated PECAM-1 antibody specific for CD 31 (1:100 dilution, clone MEC 13.3, Pharmingen, San Diego, Calif.) was used to detect endothelial cells and dc101 monoclonal antisera (Imclone, New York, N.Y.) was used to detect flk-1. Polyclonal antisera specific for BDNF, NT-3, NT-4 (sc-546, sc-547, sc-545 respectively, 1:50-1:500 dilution, Santa Cruz Immunochemicals, Santa Cruz, Calif.) or kinase active trk B (sc-12-G, 1:100 dilution, Santa Cruz Immunochemicals, Santa Cruz, Calif.) were used on tissues which had been snap frozen over liquid nitrogen vapor and sectioned on a cryostat. The specificity of neurotrophin antisera has been previously confirmed by the absence of staining of neural tissues from the appropriate gene targeted mice. In addition, preincubation of polyclonal antisera with the immunizing peptide was used to confirm antibody specificity. Sections were treated with 0.1% hydrogen peroxide prior to incubation with the primary antibody, and signal amplification utilized the avidin:biotinylated horseradish peroxidase complex method (ABC Vectastain, Vector Labs, Burlingame, Calif.). TUNEL procedure was performed as per the manufacturer's recommendation (BoeringerManheim, Chicago, Ill.) using frozen sections. Double immunofluorescence microscopy was performed using a Zeiss Axioskop microscope (Thornwood, N.Y.), or a Zeiss confocal microscope (Thornwood, N.Y.) to generate 0.5 micron optical sections.

Example 3

Generation of NesPIXpBDNF Mice

The generation of transgenic mice has been described earlier (Ringstedt et al., "BDNF Regulates Reelin Expression and Cajal-Retzius Cell Development on the Cerebral Cortex," *Neuron* 21:299-310 (1998), which is hereby incorporated by reference). Briefly, the Nes PIX-pBDNF construct consisted of a region extending 5.8 kb upstream from the initiation codon of the mouse nestin gene followed by a 1 kb fragment from the fifth exon of the mouse gene containing the complete BDNF protein coding sequence, a 300 bp long SV40 polyadenylation signal, and 5.4 kb of the nestin gene downstream sequence including introns 1, 2 and 3. The construct was injected into fertilized mouse oocytes that were subsequently transplanted into pseudopregnant females. Embryos were harvested at E17.5-E18.5 from staged pregnant mothers, and were decapitated and the thoracic contents were dissected and either fixed in 4% paraformaldehyde prior to embedding in paraffin, or snap frozen over liquid nitrogen prior to frozen sectioning. Head tissue was used for genotyping using PCR as described (Ringstedt et al., "BDNF Regulates Reelin Expression and Cajal-Retzius Cell Development on the Cerebral Cortex," *Neuron* 21:299-310 (1998), which is hereby incorporated by reference).

Example 4

Capillary Counts

Immunohistochemistry was performed on heart sections using the biotinylated anti-CD-31 antisera which detects all vascular endothelial cells (Gerber et al., "VEGF is Required for Growth and Survival in Neonatal Mice," *Development* 126:1149-1159 (1999), which is hereby incorporated by reference). Immunostained sections were photographed at 400×, and images were imported and analyzed using NIH Image. Subepicardial regions were randomly selected and the area of immunoreactivity was quantitated and expressed as a percent of the total area analyzed. Three independent fields were counted from each heart section obtained, using tissue from three transgenic and three wildtype littermates.

Example 5

Cell Culture

Microvascular endothelial cells were isolated from the hearts of C57/Bl mice at postnatal day 2-4 according to established protocols (Lodge et al., "A Simple Method of Vascular Endothelial Cell Isolation," *Transplantation Proceedings* 24:2816-2817 (1992), which is hereby incorporated by reference). In brief, minced hearts were digested with collagenase and DNAse 1, and cells plated on gelatin coated plates. Endothelial cells were released by brief trypsinization after 48 hours in culture, and maintained on gelatin coated plates in DMEM/F12 media containing 5% fetal bovine serum, 0.1% mouse serum, insulin, transferrin, and selenium (1:100, Gibco, Rockville, Md.) and used at passage 1 or 2. Using this procedure, approximately $0.5-1\times10^6$ cells were isolated from 20 neonatal hearts, and cell purity was quantitated using acetylated LDL binding and CD-31 expression assessed by flow cytometric analysis as described (Bergers et al., "Effects of Angiogenesis Inhibitors on Multistage Carcinogenesis in Mice," *Science* 284:808-812 (1999), which is hereby incorporated by reference). For TUNEL analysis, $4\times10^4$ cells/cm$^2$ were plated on gelatin coated Permanox slides (Nalgene Nunc, Naperville, Ill.)) and were cultured as above for 24 hours. Cells were washed and re-fed with X-vivo containing 0% serum±the indicated growth factor, or in X-vivo20 (Biowhittaker, Walkersville, Md.) containing 10% serum for 48 hours prior to fixation and TUNEL assessment. 1500 cells in each well were scored for TUNEL positivity. For assessment of annexin V binding, cells were deeded onto gelatin coated 6 will plates and cultured as above with the addition of 1 nl/ml of bFGF to the media. After 24 hours, cells were washed, and re-fed with X-vivo20 containing 0% serum and additional growth factors as indicated, or X-vivo20 containing 10% serum. After 48 hours, cell suspensions were generated using PBS/EDTA, washed in serum free DMEM and annexin V binding was determined by incubating the cells with FITC-conjugated Annexin V (Immunotech, Miami, Fla.) in DME containing 1.5 mM Ca$^{2+}$ on ice for ten minutes.

After washing to remove unbound annexin V, cells were incubated with propidium iodide and cell samples analyzed by flow cytometry using a Coulter Elite system (Miami, Fla.).

Example 6

RT-PCR

Total RNA was extracted from microvascular EC (passage 4-5) and from adult murine brain as described (Chomczynski et al., "Single-Step Method of RNA Isolation by Acid Guanidinium Thiocyanate-Phenol-Chloroform Extraction," *Anal Biochem* 162:156-159 (1987), which is hereby incorporated by reference). One microgram of total RNA was subjected to reverse transcription using murine leukemia virus transcriptase (Perkin-Elmer, Branchburg, N.J.). Total RNA not incubated with reverse transcriptase was used a negative control. RT-PCR was performed using primer sequences for BDNF or truncated trk B as described (Labouyrie et al., "Expression of Neurotrophins and their Receptors in Human Bone Marrow," *Am. J. Pathol.* 154:405-415 (1999), which is hereby incorporated by reference). Primer sequences for kinase active trk B were modified from Labourie et al., "Expression of Neurotrophins and their Receptors in Human Bone Marrow," *Am. J. Pathol.* 154:405-415 (1999), which is hereby incorporated by reference, to reflect codon usage in the murine sequence. The PCR products were resolved by electrophoresis in 7% acrylamide gels, followed by visualization with ethidium bromide.

Example 7

Echocardiographic Imaging

Within 48 hours of birth, all animals in a litter were subjected to sonographic imaging in a blinded fashion. Animals were imaged by placement of a 40 MHz Scimed coronary probe (Boston Scientific Scimed, Minneapolis, Minn.) in warmed gel on the anterior chest wall, using a Clear View Ultra Boston Scientific system (model 15006, Minneapolis, Minn.) with real time image analysis. Images of the short axis and long axis of the heart were identified, and imaging proceeded for a minimum of four minutes per animal. The cardiac rate, chamber dimensions, and wall motion were determined on each animal by analysis of recorded images, using the Diagnostic Off-line analysis system (Diagnostics, Inc., Houston, Tex.). The animals were sacrificed for genotyping and histologic analysis within 4 hours of imaging.

Example 8

BDNF and trk B are Expressed by Vessels in Adult and Embryonic Rodent Heart

Figure 1B:
Figure 1C:
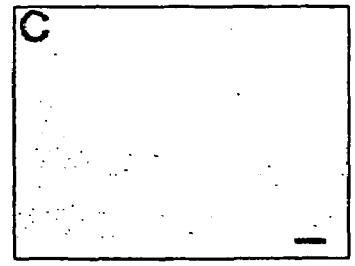
Figure 1D:
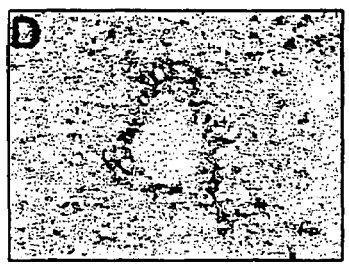
Figure 1E:
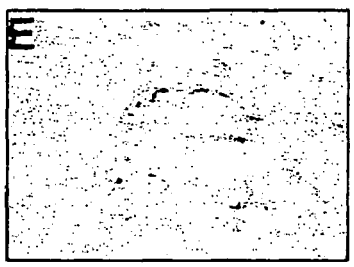
Figure 1F:
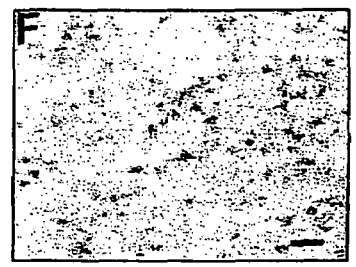
Figure 1G:
Figure 1H:
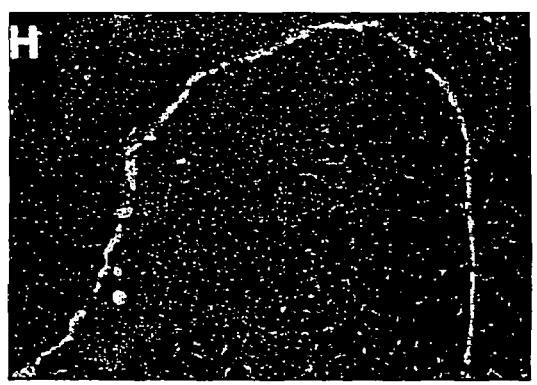
Figure 1I:
Figure 1J:
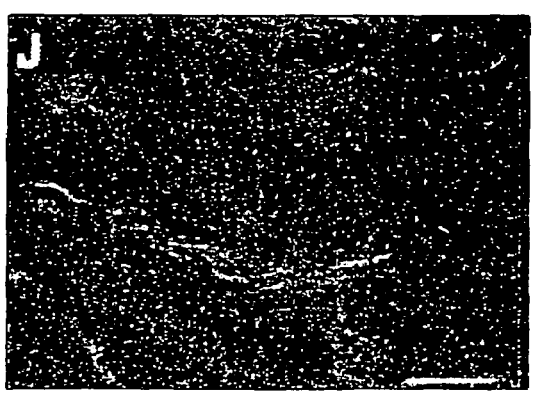

The expression of BDNF and related neurotrophins in uninjured, non-ischemic adult rodent heart was assessed immunohistochemically. BDNF is expressed by endothelial cells lining muscular arteries and arterioles and a proportion of intramyocardial capillaries (FIG. 1A), whereas the related neurotrophin, NT-3, is most highly expressed by capillaries in adult rodent heart (FIG. 1B). Previous studies have demonstrated that NT-4 mRNA is expressed at significant levels in the embryonic rat heart but falls to undetectable levels in the adult rodent heart (Timmusk et al., "Widespread and Developmentally Regulated Expression of Neurotrophin-4 mRNA in Rat Brain and Peripheral Tissues," *Eur. J. Neurosci* 5:605-613 (1993), which is hereby incorporated by reference), and are consistent with an inability to detect NT-4 protein in adult rodent heart sections (FIG. 1C). In the late gestational rodent heart, BDNF and the kinase active isoform of trk B are localized to intramyocardial vessels (FIGS. 1D, E, and control FIG. 1F). Using double immunofluorescence and confocal microscopy, BDNF and trk B co-localize with the endothelial marker, CD 31 (PECAM), suggesting that endothelial cells express both receptor and ligand in the adult heart (FIGS. 1G and H) and in late gestation at embryonic day E18.5 (FIGS. 1I and J). The similar patterns of expression of BDNF and trk B with CD 31 suggests that BDNF and trk B co-localize in the developing intramyocardial arteries in late gestation, and expression of this ligand:receptor system by intramyocardial vessels persists into adulthood.

Example 9

Vascular Defects in BDNF (−/−) Mice

Figure 2A:
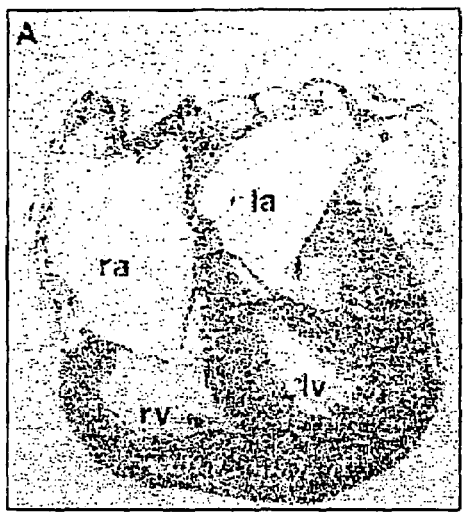
FIGS. 2A-H show that BDNF (−/−) animals exhibit hemorrhage within the ventricular walls through histological analyses of hearts of animals sacrificed within 8 hours of birth. Panels A, B, C, and D are sections stained with hematoxylin and eosin. ra and la=right and left atria; rv and lv=right and left ventricles; asd=atrial septal defect. Panels E, F, G, and H show thin sections of Epon embedded, toluidine blue stained tissues from P0 animals. Note the abnormal arteriole, but normal venule in the BDNF (−/−) sections. Panels A, C, E, and G are BDNF (+/+) animals. Panels B, D, F, and H are BDNF (−/−) animals. Bars, 150 μm (panels A and B); 50 μm (panels D, E, and F); 5 μm (panels G and H).
Figure 2B:
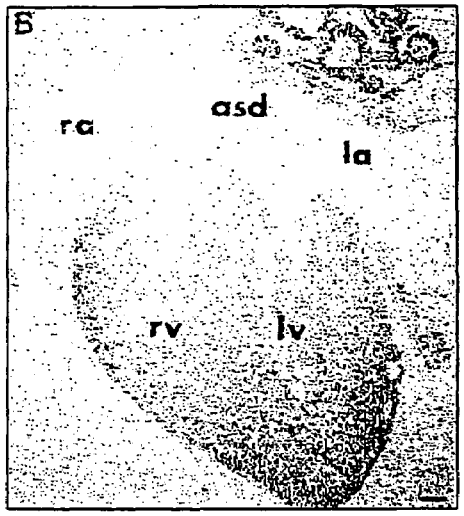
Figure 2C:
Figure 2D:
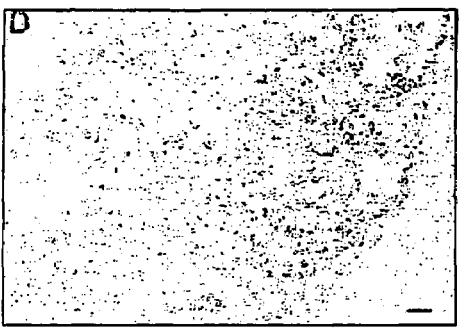

To determine whether BDNF performs a critical role in mammalian cardiac or vascular development, the hearts of mice with targeted deletion of the BDNF gene were examined. BDNF null mutant (−/−) mice exhibit well characterized losses in trk B expressing peripheral sensory neurons regulating respiratory rhythm, and in Purkinje neurons (Jones et al., "Targeted Disruption of the BDNF Gene Perturbs Brain and Sensory Neuron Development but not Motor Neuron Development," *Cell* 76:989-999 (1994); Ernfors et al., "Mice Lacking Brain-Derived Neurotrophic Factor Develop with Sensory Deficits," *Nature* 368:147-150 (1994); Erickson et al., "Mice Lacking Brain-Derived Neurotrophic Factor Exhibit Visceral Sensory Neuron Losses Distinct from Mice Lacking NT4 and Display a Severe Developmental Deficit in Control of Breathing," *J. Neurosci* 16:5361-5371 (1996); Schwartz et al., "Abnormal Cerebellar Development and Foliation in the BDNF (−/−) Mice Reveals a Role for Neurotrophins in CNS Patterning," *Neuron* 19:269-281 (1997), which is hereby incorporated by reference). The majority of BDNF (−/−) pups die within 1-4 days of birth, although approximately 10% of the animals survive for one to two weeks, with markedly reduced body weight, and impaired spontaneous movement, a phenotype suggesting potential defects in cardiovascular development. Upon gross examination of BDNF (−/−) mice at postnatal day 0 (P0), the heart size and anatomical relationships of the heart and great vessels appeared unremarkable. 14 of 15 BDNF (−/−) animals examined at P0, however, exhibited intramyocardial hemorrhage, which ranged from focal areas within the left ventricular wall, to diffuse hemorrhage within the walls of both ventricles and in the base of the atria (FIGS. 2B and D, compare to FIGS. 2A and C). Intramyocardial hemorrhage was typically confined to the more epicardial regions of the ventricular walls, and was rarely observed in the interventricular septum.

Figure 2E:
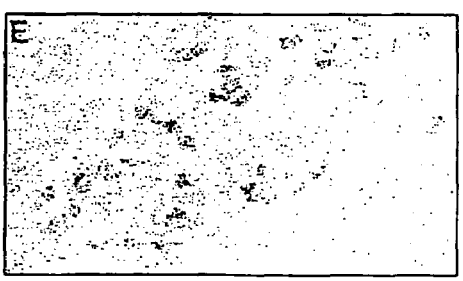
Figure 2F:
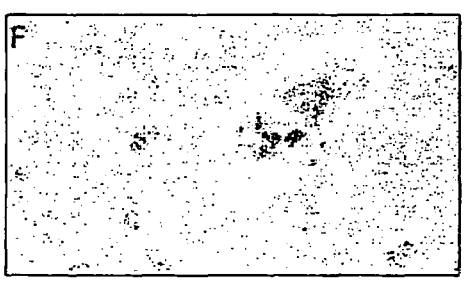

Because BDNF and trk B are expressed by late gestational and adult intramyocardial vessels, potential defects in vessel morphogenesis in the BDNF (−/−) animals were assessed by ultrastructural analysis. Abnormalities in the morphology of intramyocardial arterioles (15 of 18 vessels examined) were detected in the BDNF (−/−) animals, as compared to (+/+) littermates (16 vessels examined). These included hypertrophy and abnormal vacuolization of the endothelial cells (15 of 18 vessels), perivascular edema (9 of 18 vessels), and a modest reduction in the number of pericytes and vascular smooth muscle cells in the tunica media (10 of 18 vessels) (FIG. 2F, compare to FIG. 2E). Intramyocardial venules in both the BDNF (−/−) mice (6 vessels examined) and in BDNF (+/+) animals (5 vessels examined) appeared unremarkable (FIG.

Figure 2G:
Figure 2H:
Figure 3B:
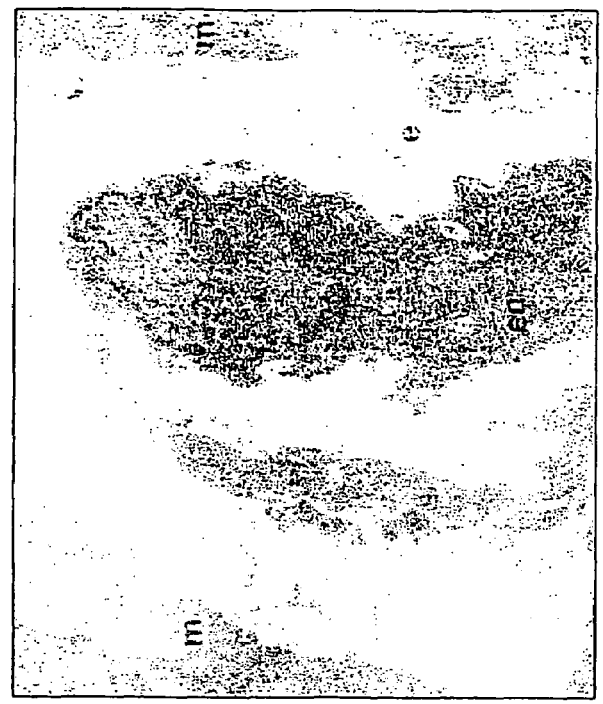
FIGS. 3A-G show endothelial cell abnormalities in BDNF (−/−) animals. Panels A, B, and C are electron microscopic analyses of the left ventricular wall from BDNF (+/+) (panel A) or (−/−) (panels B and C) P0 littermates. Vacuolated endothelial cells with an extensive and disorganized extracellular matrix were consistently detected in the capillaries and arterioles of the BDNF (−/−) animals. Panels D, E, F, and G show the use of immunofluorescence microscopy to detect PECAM (CD31) (rhodamine) and TUNEL (FITC) positivity in E18.5 embryos (panels D and E) or P2 neonates (panels F and G). Panels D and F are sections from BDNF (+/+) animals, and panels E and G are sections from BDNF (−/−) animals. c=cardiac myocyte; en=endothelial cell; e=perivascular edema. Bars, 0.4 μm (panels A and B); 0.2 μm (panel C); 30 μm (panels D, E, F, and G).
Figure 3C:
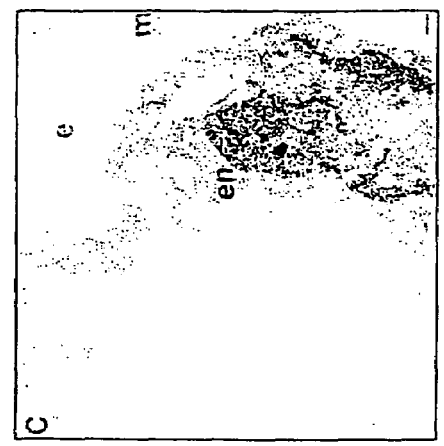
Figure 3A:

2H, compare to FIG. 2G). By electron microscopic analysis, endothelial cells within arterioles and in capillaries appeared enlarged and focally degenerated, with a vacuolated cytoplasm and prominent plasma membrane blebbing (FIGS. 3B and C, compare with FIG. 3A). More than 60% of the capillary endothelial cells examined (51 of 80) in sections of hearts from BDNF (−/−) animals (P0) exhibited cytoplasmic vacuolization, disorganization of the extracellular matrix, and perivascular edema.

Figure 3E:
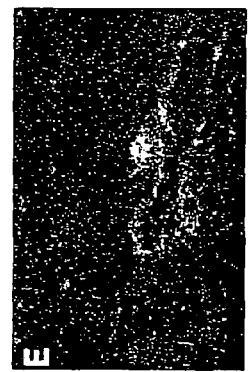
Figure 3G:
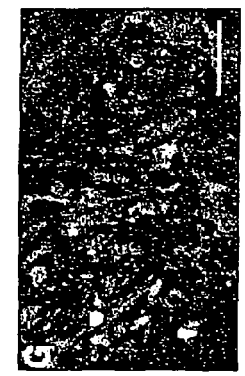
Figure 3D:
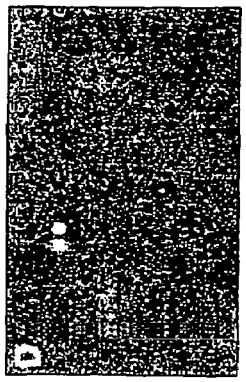
Figure 3F:
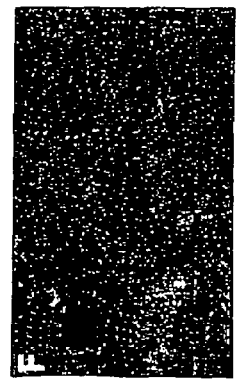
Figure 8B:
FIGS. 8A-E show en bloc analysis of Matrigel containing recombinant growth factors. Matrigel containing 50 ng/ml of the indicated growth factor, or with no growth factor addition (control), was injected subcutaneously in the region of the rectus abdominus of six week old mice. After 14 days, animals were sacrificed, and the Matrigel plug was visualized following dissection of the anterior abdominal wall (10× magnification).
Figure 8E:
Figure 8A:
Figure 8D:
Figure 8C:
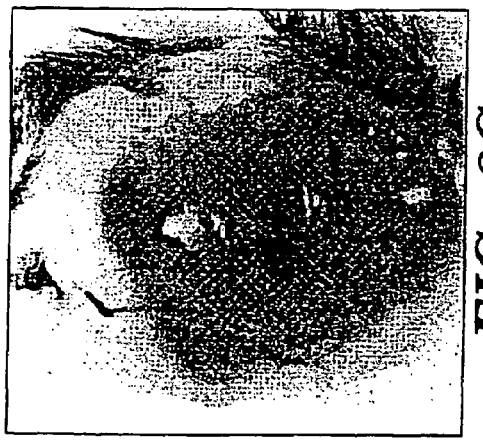
Figure 10A:
FIGS. 10A-F show histological analysis of Matrigel sections containing the indicated growth factor (at 50 ng/ml) or no additional growth factor (control). Following paraformaldehyde fixation, paraffin embedded tissue was sectional at 10 microns, and processed with hematoxylin and eosin staining. A minimum of 7 mm of tissue was analyzed in serial section analysis and representative sections were photographed at the indicated magnifications (left panels: 40×; right panels: 160×).
Figure 10B:
Figure 10C:
Figure 10D:
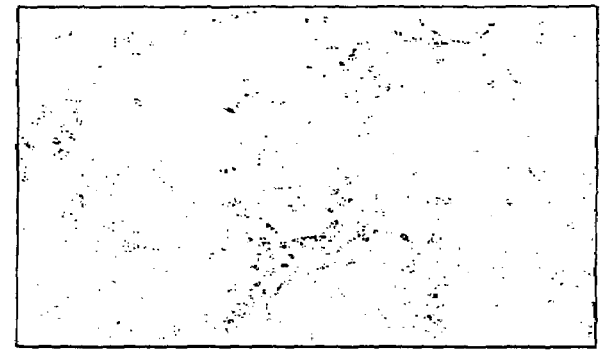
Figure 10E:
Figure 10F:

To determine whether the ultrastructural changes noted in endothelial cells reflected an apoptotic process, concomitant TUNEL analysis and CD31 immunofluorescence detection was performed using tissue sections from BDNF (−/−) animals and (+/+) littermates at E18.5 or P2 (FIGS. 3D, E, F, and G). In sections from E18.5 BDNF (−/−) hearts, numerous TUNEL positive cells were detected per low power field and the majority of these cells displayed CD31 immunoreactivity, whereas sections from (+/+) embryos exhibited many fewer TUNEL positive cells, which were CD31 negative. In examination of P2 BDNF (−/−) hearts, a marked increase in TUNEL positive cells was detected. Although the majority of TUNEL positive cells colocalized with CD31 immunodetection, in regions with high TUNEL detection, CD31 negative cells were noted as well, which may reflect myocyte apoptosis in local regions of vessel compromise. These results suggest that BDNF deprivation results in the apoptosis of endothelial cells in capillaries and arterioles of the late gestational and early neonatal heart.

To establish the onset of abnormal intramyocardial vessel formation in the BDNF (−/−) mice, 11 BDNF (−/−) embryos and 6 BDNF (+/+) littermates were examined from E11.5 to E19.5. Intramyocardial hemorrhage in BDNF (−/−) embryos could be detected first at E16.5 (2 of 2 BDNF (−/−) embryos from different litters (FIG. 4B)), and was present in 3 of 3 BDNF (−/−) embryos (FIG. 4D) examined at E17.5, and absent in BDNF (+/−) and (+/+) littermates (FIGS. 4A and C). The onset of hemorrhage in late gestation suggested that deficient BDNF expression did not impair vasculogenesis or sprouting angiogenesis, as gene targeted embryos with defects in these processes typically die in utero between embryonic day 9-13 (Carmeliet et al., "Abnormal Blood Vessel Development and Lethality in Embryos Lacking a Single VEGF Allele," *Nature* 380:435-439 (1996); Fong et al., "Role of the Flt-1 Receptor Tyrosine Kinase in Regulating Assembly of Vascular Endothelium," *Nature* 376:66-70 (1995); Shalaby et al., "Failure of Blood-Island Formation and Vasculogenesis in FLK-1-Deficient Mice," *Nature* 376:62-66 (1995), which are hereby incorporated by reference). Indeed, the density and patterning of the intramyocardial capillary bed in the BDNF (−/−) embryos at E18.5 was not distinguishable from that of BDNF (+/+) littermates as assessed by CD31 immunoreactivity (FIGS. 4G and H). These results suggest that sprouting angiogenesis proceeds normally in the hearts of BDNF (−/−) embryos during mid to late gestation.

Example 10

Echocardiographic Imaging of BDNF (−/−) Mice

To assess the functional impairment of the BDNF deficient heart in vivo, real time echocardiography was performed on littermates within 48 hours of birth using a 40 MHz intravascular ultrasound catheter for transthoracic images. Three of three BDNF (−/−) animals that were imaged displayed significant decreases in left ventricular ejection fraction (EF) as compared to normal littermates (see Tables 1 and 2, below).

TABLE 1

Ejection fractions for two BDNF (−/−) and three BDNF (−/−) animals from two litters.

| BDNF (+/+) | BDNF (−/−) |
|---|---|
| 73% | 42% |
| 77% | 62% |
|  | 31% |

TABLE 2

Representative measurements from BDNF (+/+) and BDNF (−/−) littermates.

|  | BDNF (+/+) | BDNF (−/−) |
|---|---|---|
| 1 vidd | 1.10 mm | 1.20 mm |
| 1 vids | 0.70 mm | 1.00 mm |
| dias vol | 1.33 mm$^3$ | 1.73 mm$^3$ |
| sys vol | 0.34 mm$^3$ | 1.00 mm$^3$ |
| stroke volume | 0.99 mm$^3$ | 0.73 mm$^3$ |
| ejection fraction | 73% | 42% |

The reduction in ejection fraction in the BDNF deficient neonates is consistent with the histologic and ultrastructural evidence of intramyocardial vessel fragility and hemorrhage which impacts on myocardial contactility.

Example 11

Deficiency in BDNF Results in Defective Atrial Septation

In addition to vascular defects, microscopic examination of BDNF (−/−) animals was notable for abnormalities in atrial septation in 10 of the 12 animals examined by serial section analysis at P0 (FIG. 2B). In the affected animals, the septum primum appeared to be largely vestigial, while the septum secundum exhibited varying degrees of hypoplasia. The result of these defects is incompetence of the foramen ovale with a prominent atrial septal defect involving both the septum primum and secundum. By morphometric analysis, atrial septal defects in excess of 100 microns in the anterior-posterior plane were detected in four of the BDNF (−/−) animals. No atrial septal defects were detected in the 10 BDNF (+/−) or (+/+) littermates examined (FIG. 2A). Marked atrial enlargement and atrial wall thinning, with concomitant pulmonary congestion and occasional intra-alveolar hemorrhage were noted in the 10 BDNF (−/−) animals with atrial septal defects. No defects in ventricular septal formation or in valvulogenesis were detected. Furthermore, ventricular trabeculation and septal muscle formation were unremarkable.

To establish the onset and mechanisms underlying defective atrioseptal formation observed at P0, BDNF (−/−) embryos and (+/+) littermates were examined from E11.5 to E18.5 (FIG. 4). The formation of the dorsal component of the septum primum is initiated between E10.5 and E11.5 (Kaufman, "The Atlas of Mouse Development," *Academic Press, Inc.*, San Diego (1992), which is hereby incorporated by reference, a process which appears unaffected by deficient BDNF expression (FIGS. 4A and B). However, by E14.5, a stage at which the septum primum has formed, and the dorsal and ventral ridges of the septum secundum are emerging in wild-type animals, the BDNF (−/−) littermates exhibit hypoplasia of the developing dorsal and ventral components of the septum secundum (FIGS. 4C and D). The hypoplasia of the septum secundum in the BDNF (−/−) embryos is progressive at gestational stages E16.5 and E18.5 (FIG. 4F), and results in incompetence of the foramen ovale at P0 (FIG. 2B). To determine whether abnormalities in BDNF mediated trk B signaling could result in the observed septal hypoplasia, immunohistochemical localization of the kinase active trk B and BDNF in the developing atria was undertaken. Expression of the kinase active trk B receptor and BDNF expression is detectable in the endocardium of the developing atria, in the region of the septum primum (FIGS. 4I and J). These results suggest that BDNF-mediated trk B signaling is required for the persistence and continued growth of the atrial septum primum and septum secundum.

Example 12

BDNF Effects on Purified Cardiac Microvascular Endothelial Cells

To confirm the direct actions of BDNF on endothelial cells, cultures of highly purified neonatal microvascular cardiac endothelial cells were obtained from wild-type mice. The purity of the cell cultures was quantitated by flow cytometric analysis of CD31 (PECAM) expression and uptake of DiI-LDL, and was routinely determined to be greater than 95% (FIG. 6A). Using RT-PCR analysis, BDNF mRNA expression was detectable in samples from cardiac microvascular endothelial cells (FIG. 6C), extending recent studies documenting BDNF expression by brain microvascular endothelial cells (Leventhal et al., "Endothelial Trophic Support of Neuronal Production and Recruitment From the Adult Mammalian Subependyma," *Mol. Cell. Neurosci.* 13:450-464 (1999), which is hereby incorporated by reference). Low passage cardiac microvascular endothelial cells consistently express transcripts for kinase active trk B (FIG. 6C), using well characterized primer sets to detect trk B isoforms (Labouyrie et al., "Expression of Neurotrophins and Their Receptors in Human Bone Marrow," *Am. J. Pathol.* 154:405-415 (1999), which is hereby incorporated by reference). Transcripts for truncated trk B receptors lacking kinase activity were occasionally detected from RNA obtained from higher passage cells.

Although deficient expression of BDNF in vivo results in endothelial cell apoptosis (as above, FIG. 3E), it is desirable to assess whether BDNF acts directly upon endothelial cells to support survival under conditions of serum deprivation. Using cultured microvascular cardiac endothelial cells, nanomolar concentration of BDNF was capable of maintaining endothelial cell viability, as quantitated using a LIVE/DEAD assay. To confirm that BDNF was able to inhibit the endothelial cell apoptosis induced by serum withdrawal, quantitation of apoptosis was undertaken using TUNEL analysis and annexin V binding (FIGS. 6D, E, F, and G). Moreover, nanomolar concentrations of BDNF were effective in reducing by approximately fifty percent the cellular apoptosis of cardiac microvascular endothelial cell followed by serum withdrawal (FIG. 6F, compare with FIG. 6E). BDNF treatment resulted in a 50% reduction in annexin V binding, relative to serum deprived cells (FIG. 6G), and was as effective as VEGF in maintaining cell viability. The ability of BDNF to maintain the survival of purified populations of cardiac microvascular endothelial cells suggests direct actions of this growth factor on this trk B expressing cell population.

Example 13

BDNF Overexpression in the Gestational Heart Induces Angiogenesis

To determine whether excess levels of BDNF may result in vascular abnormalities during embryogenesis, transgenic mice overexpressing BDNF under the control of the promoter and enhancer regions of the nestin gene were generated. These mice used enhancer sequences in intron 1, which direct expression in developing muscle, and sequences in intron 2 which are required for expression in the developing nervous system (Zimmerman et al., "Independent Regulatory Elements in the Nestin Gene Direct Transgene Expression to Neural Stem Cells or Muscle," *Neuron* 12:11-24 (1994), which is hereby incorporated by reference). As these mice die shortly before birth (Ringstedt et al., "Role of Brain-Derived Neurotrophic Factor in Target Invasion in the Gustatory System," *J. Neurosci* 19:3507-3518 (1999), which is hereby incorporated by reference), transgenic embryos (E 17.5-E18.5) arising from independent injections of the construct were harvested and found to focally overexpress BDNF in the cardiac ventricular walls (FIG. 7F, compare with FIG. 7D). Histologic analysis of the hearts from 6 BDNF overexpressing or 6 wild type embryos revealed focal abnormalities in the ventricular wall of transgenic animals, characterized by an increased number of predominantly small diameter vessels (less than 10 microns), which appeared devoid of a surrounding smooth muscle cell investment (FIG. 7B, compare with FIG. 7A). Immunohistochemistry for the endothelial cell marker CD31 revealed a 2-3 fold increase in the density of endothelial lined vessels in these regions of the ventricles of transgenic, as compared to nontransgenic littermates (FIG. 7H, compare with FIG. 7G). No differences in immunopositivity for α-actinin, a vascular smooth muscle cell marker (Hungerford et al., "Identification of a Novel Marker for Primordial Smooth Muscle and its Differentiation Expression pattern in Contractile vs. Noncontractile Cells," *J. Cell Biol.* 137:925-937 (1997), which is hereby incorporated by reference), were detected, suggesting that these vessels were capillaries (FIGS. 7I and J). To determine whether the increases in vessel number reflected increased endothelial cell proliferation, immunohistochemical detection of proliferating cell nuclear antigen (PCNA) was undertaken (FIGS. 7K and L). No differences in PCNA positivity were detected in transgenic, as compared to wild-type embryos, suggesting that BDNF overexpression promotes endothelial cell survival, rather than cell proliferation in vitro. Significantly, no evidence of intraventricular wall hemorrhage was noted in the BDNF overexpressing embryos suggesting that BDNF does not induce vascular permeability.

Example 14

Expression of BDNF is Required for the Stabilization of Intramyocardial Vessels During Late Embryogenesis The above data demonstrate that expression of BDNF is required for the stabilization of intramyocardial vessels during late embryogenesis, through direct actions on endothelial cells. Unlike well characterized angiogenic factors, such as VEGF, which initiate vasculogenesis and sprouting angiogenesis, BDNF appears to act at later stages of arteriolar and capillary formation to maintain vessel integrity. BDNF does not appear to regulate vasculogenesis, the patterning of the intra-embryonic vessels, or sprouting angiogenesis, the initial development of capillaries from these primitive channels, as BDNF (−/−) embryos appear normal through E14.5. Unlike mice deficient in VEGF or the VEGF receptors flk-1 or flt-1, which die between E8.5 and E11.5 with severe defects in vasculogenesis, angiogenesis, and yolk sac hematopoiesis (Carmeliet et al., "Abnormal Blood Vessel Development and Lethality in Embryos Lacking a Single VEGF Allele," *Nature* 380:435-439 (1996); Fong et al., "Role of the Flt-1 Receptor Tyrosine Kinase in Regulating the Assembly of Vascular Endothelium," *Nature* 376:66-70 (1995); Shalaby et al., "Failure of Blood Island Formation and Vasculogenesis in the Flk-1 Deficient Mice," *Nature* 376:62-66 (1995), which is hereby incorporated by reference), BDNF deficient mice display normal vascular patterning and capillary branching. The vascular abnormalities in the BDNF deficient mouse are also distinctive from those exhibited by animals deficient in expression of angiopoietin-1 and its receptor tyrosine kinase Tie2. Animals lacking expression of angiopoietin-1 or Tie2 exhibit severe defects in capillary branching, and an inability to remodel the capillary network to form arteries (Sato et al., "Distinct Roles of the Receptor Tyrosine Kinases Tie-1 and Tie-2 in Blood Vessel Formation," *Nature* 376:70-74 (1995); Suri et al., "Requisite Role of Angiopoeitin-1, a Ligand for the Tie-2 Receptor, During Embryonic Angiogenesis," *Cell* 87:1171-1180 (1996), which is hereby incorporated by reference). Although ultrastructural analysis of vessels from the angiopoietin-1 and Tie 2 null mutant animals demonstrates endothelial cell degeneration, the earlier embryonic lethality of these animals at E10.5-E12, and the widespread vessel abnormalities distinguish the effects of angiopoietin-1 from BDNF.

Recent studies have identified several angiogenic factors which function to modulate reciprocal interactions between endothelial cells and the mesenchymally-derived pericyte and vascular smooth muscle cells. These mesenchymal cells are recruited during the process of vascular remodeling and are important in vessel stabilization (Risau, "Mechanisms of Angiogenesis," *Nature* 386:671-674 (1997); Darland et al., "Blood Vessel Maturation: Vascular Development Comes of Age," *J. Clin. Invest.* 103:167-168 (1999); Yancopoulos et al., "Vasculogenesis, Angiogenesis and Growth Factors: Ephrins Enter the Fray at the Border," *Cell* 93:661-664 (1998), which is hereby incorporated by reference). PDGF-BB and HB-EGF synthesized by the endothelial cells recruit pericytes and smooth muscle cells to the developing tunica media, and deficient PDGF-BB production results in defective vascular ensheathment by these supporting cell types (Lindahl et al., "Pericyte Loss and Microaneurysm Formation in the PDGF-B-deficient mice," *Science* 277:242-245 (1997), which is hereby incorporated by reference). The vascular smooth muscle cells, in turn, synthesize and secrete angiopoietin-1 to activate Tie2 receptors on the adjacent endothelial cells, resulting in bidirectional signaling between endothelial cells, and the support cells which ensheath them (Yancopoulos et al., "Vasculogenesis, Angiogenesis and Growth Factors: Ephrins Enter the Fray at the Border," *Cell* 93:661-664 (1998), which is hereby incorporated by reference). The co-localization of BDNF and trk B to endothelial cells of intramyocardial arteries and capillaries, as well as the ability of BDNF to support the survival of cardiac microvascular endothelial cells in culture provide mechanistic evidence of direct actions of BDNF on endothelial cells. In addition, ultrastructural analysis of BDNF deficient animals documenting endothelial cell degeneration and apoptosis within intramyocardial capillaries suggest that this growth factor exerts important roles in endothelial cell survival. The extent of endothelial cell vacuolization and degeneration observed in the BDNF deficient mice could result in deficient local production of growth factors such as PDGF-BB, thus secondarily impairing smooth muscle cell ensheathment and survival.

The vascular phenotype observed upon BDNF overexpression in the gestational heart further supports the hypothesized role of BDNF as a factor regulating endothelial cell survival and vessel stabilization. Although these animals exhibited increased capillary density, no hemorrhage of these vessels was observed, distinguishing the effects of BDNF from those of VEGF, which can promote the formation of capillaries with enhanced fragility. In addition, BDNF overexpression does not significantly alter endothelial cell proliferation, suggesting that the increased capillary density may result from enhanced cell survival during the normal processes of vessel remodeling.

The atrial septal defects in the BDNF (−/−) animals, as assessed by morphometric analysis, are considerably larger than that which has been described for secondary physiologic septal defects. The marked hypoplasia of these septal structures, as well as the local expression of trk B and the BDNF by the atrial endocardium, suggest that BDNF is required for normal septal development in addition to its present role in maintaining endothelial cell function. This structural defect may reflect either primary survival deficiencies in the mesenchymal cells of the septae or an endothelial cell dysfunction leading to increased apoptosis of these endothelial/mesenchymal derived structures. There is little known about the stages of cardiac valvuloseptal development, specifically as to what factors define competent valve formation along with appropriate septal development. The overall integrity of these structures will most likely be defined by a variety of mechanisms, including the heterogeneity of the endocardial endothelial cell, growth factors of the TGFβ family, and transcription factors of the Helix-Loop-Helix family (Fishman et al., "Fashioning the Vertebrate Heart: Earliest Embryonic Decisions," *Development* 124:2099-2117 (1997); Schott et al., "Congenital Heart Disease Caused by Mutations in the Transcription Factor NKX 2.5," *Science* 281:108-111 (1998), which is hereby incorporated by reference). Interestingly, the co-existence of a competent valve system in conjunction with markedly hypoplastic septal structures in the BDNF −/− animals supports an even more complicated profile of pathways that define this period of heart development.

Are there additional actions, however, for BDNF on vascular smooth muscle cells? Several studies (Nemoto et al., "Gene Expression of Neurotrophins and Their Receptors in Cultured Rat Vascular Smooth Muscle Cells," *Biochem. Biophys. Res. Commun* 245:284-288 (1998); Scarisbrick et al., "Coexpression of the mRNAs for NGF, BDNF and NT-3 in the Cardiovascular System of Pre and Post Natal Rat," *J. Neurosci.* 13:875-893 (1993), which is hereby incorporated by reference) have documented low levels of expression of BDNF in vascular smooth muscle cells from large adult vessels such as the aorta, and prior studies have documented increased expression of both BDNF and trk B by neointimal cells following vascular injury (Donovan et al., "Neurotrophin and Neurotrophin Receptors in Vascular Smooth Muscle Cells: Regulation of Expression in Response to Injury," *A. J. Path.* 147:309-324 (1995), which is hereby incorporated by reference). Migration of medial smooth muscle cells is a primary response to vascular injury, and direct chemotactic actions of neurotrophins on the trk receptor expressing adult vascular smooth muscle cells has been demonstrated. These results suggest that neurotrophins can mediate direct effects on vascular smooth muscle cells in adult, large vessels in pathologic models of injury. Although overexpression of BDNF in the developing heart does not lead to enhanced arteriolar formation, or abnormal intramyocardial vessel ensheathment, further studies will be needed to determine whether BDNF can mediate direct chemotactic or survival effects on pericytes or vascular smooth muscle cells in other vascular beds.

Although endothelial cells line vessels in all organs, local expression of growth factors which regulate endothelial cell function can confer specialization and functional heterogeneity on distinctive great vessels and the vascular beds (Edelberg et al., PDGF Mediates Cardiac Microvascular Communication," *J. Clin. Invest.* 102:837-843 (1998), which is hereby incorporated by reference). The above analysis of the BDNF (−/−) mice reveals gross hemorrhage only in the heart and lungs, with normal development of the great vessels, and of vessels within other organs such as the kidney and brain. Two distinct mechanisms could result in the limited hemorrhage in BDNF (−/−) animals: (1) expression of an alternate trk B ligand or (2) restricted, regional expression of BDNF and trk B in the developing embryo. Although BDNF is a selective and specific ligand for trk B, an alternative ligand, NT-4, is widely expressed during embryogenesis and in the adult (Timmusk et al., "Widespread and Developmentally Regulated Expression of Neurotrophin-4 mRNA in Rat Brain and Peripheral Tissues," *Eur. J. Neurosci.* 5:605-613 (1993), which is hereby incorporated by reference). In the nervous system, studies of BDNF, NT-4, and BDNF/NT-4 double null mutant mice suggest that the functions of these ligands during the development of the peripheral nervous system are partially overlapping (Jones et al., "Targeted Disruption of the BDNF Gene Perturbs Brain and Sensory Neuron Development But Not Motor Neuron Development," *Cell* 76:989-999 (1994); Ernfors et al., "Mice Lacking Brain-Derived Neurotrophic Factor Develop with Sensory Deficits," *Nature* 368: 147-150 (1994); Erickson et al., "Mice Lacking Brain-Derived Neurotrophic Factor Exhibit Visceral Sensory Neuron Losses Distinct From Mice Lacking NT4 and Display a Severe Developmental Deficit in Control of Breathing," *J. Neurosci.* 16:5361-5371 (1996), which is hereby incorporated by reference). During gestation, most non-neuronal tissues express both BDNF mRNA and NT-4 mRNA although local expression of both trk B ligands is largely reciprocal in the adult (Timmusk et al., "Widespread and Developmentally Regulated Expression of Neurotrophin-4 mRNA in Rat Brain and Peripheral Tissues," *Eur. J. Neurosci.* 5:605-613 (1993), which is hereby incorporated by reference). The developing heart, in contrast, expresses predominately NT-4 mRNA until late gestation, when BDNF mRNA expression increases significantly. Thus, the vascular defects in BDNF (−/−) animals may be limited to those organs which express one ligand selectively. Surprisingly, no abnormalities were detected in the developing hearts of NT-4 deficient mice. However, prior studies have demonstrated that circulating platelets express high levels of BDNF (Yamamoto et al., "Human Platelets Contain Brain-Derived Neurotrophic Factor," *J. Neurosci* 10:3469-3478 (1990), which is hereby incorporated by reference), which may be sufficient to maintain endothelial cell integrity and survival.

Alternatively, the relatively restricted pattern of BDNF and trk B expression to endothelial cells lining some capillaries and intramyocardial arterioles, and the partially overlapping expression of NT-3 by capillary endothelial cells, suggests that arteriolar and capillary endothelial cells may require distinct, but related growth factors to ensure cell survival. The recently described heterogeneity of cardiac microvascular endothelial cell responsiveness to PDGF-AB, and the ability of PDGF-AB to selectively regulate endothelial cell gene expression, suggests that local expression of selective growth factors can regulate microvascular endothelial cell function (Edelberg et al., (PDGF Mediates Cardiac Microvascular Communication," *J. Clin. Invest.* 102:837-843 (1998), which is hereby incorporated by reference). In addition, the recent identification of ephrin B2 and its receptor Eph B4 as embryonic markers for endothelial cells within arterial or venous capillaries, respectively, suggests that endothelial cells are molecularly distinct prior to their ensheathment by vascular smooth muscle cells (Wang et al., "Molecular Distinction and Angiogenic Interaction Between Embryonic Arteries and Veins Revealed by Ephrin-B2 and its Receptor Eph-B4," *Cell* 93:741-753 (1998), which is hereby incorporated by reference). One hypothesis to account for the patterns of expression of the neurotrophins by vascular endothelial cells is that production of the neurotrophins may be regulated by ephrin-B2:Eph-B4, or PDGF-AB mediated inter-endothelial signaling, questions most amenable to genetic dissection.

Example 14

Angiogenesis by the trk Receptor Ligands

To assess the potential actions of trk receptor ligands in initiating angiogenesis in non-ischemic tissues, a well established, non-ischemic in vivo Matrigel model system was utilized (Passaniti et al., "A Simple Quantitative Method for Assessing Angiogenesis and Antiangiogenic Agents Using Reconstituted Basement Membrane, Heparin, and Fibroblast Growth Factor," *Lab. Invest.* 67:519-528 (1992), which is hereby incorporated by reference). Young adult female mice were injected subcutaneously with 0.3 ml of growth factor depleted Matrigel (Bector Dickenson, Bedford, Mass.) containing 64 U/ml heparin and either rhVEGF (Upstate Biotechnologies, Lake Placid, N.Y.) (30-50 ng/ml), rhBDNF (50-100 ng/ml), rhNT-4 (50-100 ng/ml), or rhNT-3 (50-100 ng/ml), or no growth factor addition (rhBDNF, rhNT-4, and rhNT-3 from Promega, Madison, Wis.). After 14 days, the animals were sacrificed, and the Matrigel plug isolated, photographed, and processed for immunohistochemical and histochemical analysis (see FIGS. 8-10). Serial sections were analyzed in a blinded manner for each Matrigel plug, and the degree of cellularity was quantitated in central regions of Matrigel. Seven of eight Matrigel samples containing no additional growth factors exhibited low cellularity. In contrast, Matrigel plugs containing VEGF were highly cellular in ten of twelve animals. Matrigel containing trk ligands also yielded highly cellular sections; specifically, Matrigel containing BDNF gave rise to highly cellular sections in seven of nine animals, Matrigel containing NT-4 was highly cellular in eight of nine animals, and Matrigel containing NT-3 was highly cellular in five of seven animals.

Sections from Matrigel containing VEGF, BDNF, NT-3, NT-4, or no additional growth factor were examined from 45 animals. Microscopically the control Matrigel plug experiments yielded absent to few numbers of infiltrating endothelial cells admixed with some scattered mesenchymal cells. By comparison, the Matrigel sections containing VEGF exhibited a loose, fairly organized capillary network which in some cases was composed of a dense network of endothelial type cells with focal hemorrhage. In some VEGF-containing Matrigel plugs in which the endothelial/cellular content was rather dense, there were dilated, blood filled spaces apparently lined by endothelial cells. When examining the Matrigel plugs containing either the BDNF or NT-4 there was a dramatic increase in the number of infiltrating endothelial-like cells arborizing throughout the material when compared with the controls or VEGF treated samples. In some of these cases, the dense network of cells was contained many mitotic figures and apoptotic bodies. Furthermore, in some cases, there were dilated blood filled spaces similar to those noted with the VEGF treated plugs. The NT-3 containing Matrigel samples exhibited a cellular content that was less than that exhibited by the BDNF or NT-4 Matrigel samples but was more dense when compared with the VEGF-Matrigel treated group. In all treated matrigel experiments, there were varying degrees of an inflammatory component; in the BDNF and NT-4 samples, this appeared to be composed of granulocytes including eosinophils.

Although the present invention has been described in detail for the purpose of illustration, it is understood that such detail is solely for that purpose and variations can be made by those skilled in the art without departing from the spirit and scope of the invention which is defined by the following claims.

What is claimed:

1. A method of increasing capillary density in the heart of a subject, said method comprising:
    selecting a subject in need of increased capillary density in the heart and
    administering to the heart of the selected subject a trk receptor ligand in an amount effective to increase capillary density in the heart, said trk receptor ligand being selected from the group consisting of brain-derived neurotrophic factor, NT-3, and NT-4.

2. The method according to claim 1, wherein the heart of the subject has abnormal vascularity in its ventricular walls.

3. The method according to claim 1, wherein the subject has a condition treatable by increasing capillary density.

4. The method according to claim 1, wherein the trk receptor ligand is administered directly to the heart.

5. The method according to claim 1, wherein the trk receptor ligand is administered in a manner which targets it to the heart.

6. The method according to claim 1, wherein the trk receptor ligand is administered to the heart in nanomolar concentrations.

7. A method of maintaining the viability of microvascular cardiac endothelial cells in a subject, said method comprising:
    selecting a subject in need of maintaining viability of microvascular cardiac endothelial cells and
    administering to the heart of the selected subject a trk receptor ligand in an amount effective to maintain the viability of the microvascular cardiac endothelial cells in the subject, said trk receptor ligand being selected from the group consisting of brain-derived neurotrophic factor, NT-3, and NT-4.

8. The method according to claim 7, wherein the subject has a condition treatable by maintaining the viability of microvascular cardiac endothelial cells.

9. The method according to claim 7, wherein the trk receptor ligand is administered directly to the heart.

10. The method according to claim 7, wherein the trk receptor ligand is administered in a manner which targets it to the heart.

11. The method according to claim 7, wherein the trk receptor ligand is administered to the heart in nanomolar concentrations.

* * * * *